(12) United States Patent
Dischert et al.

(10) Patent No.: US 9,121,043 B2
(45) Date of Patent: Sep. 1, 2015

(54) METHOD FOR PRODUCING GLYCOLIC ACID USING AN INDUCIBLE PROMOTER

(75) Inventors: Wanda Dischert, Vic-le-Comte (FR); Rainer Figge, Le Crest (FR); Philippe Soucaille, Deyme (FR)

(73) Assignee: METABOLIC EXPLORER, Saint Beauzire (FR)

( * ) Notice: Subject to any disclaimer, the term of this patent is extended or adjusted under 35 U.S.C. 154(b) by 175 days.

(21) Appl. No.: 13/704,578

(22) PCT Filed: Jun. 15, 2011

(86) PCT No.: PCT/EP2011/059884
§ 371 (c)(1),
(2), (4) Date: Dec. 14, 2012

(87) PCT Pub. No.: WO2011/157728
PCT Pub. Date: Dec. 22, 2011

(65) Prior Publication Data
US 2013/0089903 A1    Apr. 11, 2013

Related U.S. Application Data

(60) Provisional application No. 61/354,887, filed on Jun. 15, 2010.

(30) Foreign Application Priority Data

Jun. 15, 2010   (EP) .................................. 10305635

(51) Int. Cl.
*C12P 7/42* (2006.01)
*C12N 15/70* (2006.01)
*C12N 15/63* (2006.01)

(52) U.S. Cl.
CPC ................. *C12P 7/42* (2013.01); *C12N 15/635* (2013.01); *C12N 15/70* (2013.01)

(58) Field of Classification Search
None
See application file for complete search history.

(56) References Cited

U.S. PATENT DOCUMENTS

| 7,445,917 | B2 | 11/2008 | DiCosimo et al. |
| 2006/0160199 | A1 | 7/2006 | DiCosimo et al. |
| 2009/0155867 | A1 | 6/2009 | Soucaille |

FOREIGN PATENT DOCUMENTS

| EP | 2025759 A1 | 2/2009 |
| EP | 2025760 A1 | 2/2009 |
| WO | 9811231 A1 | 3/1998 |
| WO | 2004020640 A2 | 3/2004 |
| WO | 2006069110 A2 | 6/2006 |
| WO | 2007005837 A2 | 1/2007 |
| WO | 2007140816 A1 | 12/2007 |
| WO | 2007141316 A2 | 12/2007 |
| WO | 2010108909 A1 | 9/2010 |
| WO | WO2007140816 | * 12/2013 |

OTHER PUBLICATIONS

International Search Report for PCT/EP2011/059884 Mailed August 24, 2011.
Orosz et al.; "Analysis of the Complex Transcription Termination Region of the *Escherichia coli* RRND Gene"; Eur. J. Biochem.; 1991; vol. 201; pp. 653-659; FEBS.
Schaefer et al.; "Automated Sampling Device for Monitoring Intracellular Metabolite Dyamics"; Analytical Biochemistry; 1999; vol. 270; pp. 88-96; Academic Press.
Sussman et al.; "Sur Un Systeme De Repression Thermosensible Chez Le Bacteriophage Gamma D'*Escherichia coli*"; Genetique Physiologique; Feb. 19, 1962; Academie Des Sciences; pp. 1517-1519.
Tang et al.; "Microbial Conversion of Glycerol to 1,3-Propanediol by an Engineered Strain of *Escherichia coli*"; Applied and Environmental Microbiology; Mar. 2009; vol. 75; No. 6; pp. 1628-1634; American Society for Microbiology.
Winstanley et al.; "Differential Regulation of Lambda PL and PR Promoters by a CI Repressor in a Broad-Host-Range Thermoregulated Plasmid Marker System"; Apr. 1989; vol. 55; No. 4; pp. 771-777; Applied and Environmental Microbiology; American Society for Microbiology.
Anderson; "Growth Requirements of Virus-Resistant Mutants of *Escherichia coli* Strain "B""; Communicated Mar. 21, 1946; PROC. N.A.S.; pp. 120-128; Department of Biology, Vanderbilt University.
Bukrinsky et al.; "Multicopy Expression Vector Based on Temperature-Regulated LAC Repressor: Expression of Human Immunodeficiency Virus ENV Gene in *Escherichia coli*"; Gene; 1988; vol. 70; pp. 415-417; Elsevier Science Publishers B.V.
Datsenko et al.; "One-Step Inactivation of Chromosomal Genes in *Escherichia coli* K-12 Using PCR Products"; PNAS; Jun. 6, 2000; vol. 97; No. 12; pp. 6640-6645.
Harrington et al.; "Balanced Branching in Transcription Termination"; PNAS; Apr. 24, 2001; vol. 98; No. 9; pp. 5019-5024.

(Continued)

*Primary Examiner* — Christian Fronda
(74) *Attorney, Agent, or Firm* — Miles & Stockbridge P.C.

(57) ABSTRACT

The present invention relates to use of inducible promoters in the production of glycolic acid by fermentation. The present invention concerns a method for the production of glycolic acid in a fermentative process comprising the following steps:

culturing a modified microorganism in an appropriate culture medium comprising a source of carbon, modulating in said microorganism the expression of a target gene with an external stimulus, and recovering glycolic acid from the culture medium, wherein in said modified microorganism, the expression of at least one gene involved in glycolic acid production is under the control of a heterologous inducible promoter whose activity is modulated with said external stimulus.

The invention also concerned the modified microorganism used in the method of glycolic acid production.

16 Claims, 1 Drawing Sheet

(56) References Cited

OTHER PUBLICATIONS

Kataoka et al.; "Glycolic Acid Production Using Ethylene Glycol-Oxidizing Microorganisms"; Biosci. Biotechnol.; 2001; vol. 65; No. 10; pp. 2265-2270.

Mandal et al.; "Heat-Sensitive DNA-Binding Activity of the CI Product of Bacteriophage Lambda"; Molec. Gen. Genet.; 1976; vol. 146; pp. 299-302; Springer-Verlag.

Mermet-Bouvier et al.; A Conditional Expression Vector for the Cyanobacteria Synechocystis Sp. Strains PCC6803 and PCC6714 or Synechococcus Sp. Strains PCC7942 and PCC6301; Current Microbiology; 1994; vol. 28; pp. 145-148; Springer-Verlag.

Norrander et al.; "Construction of Improved M13 Vectors Using Oligodeoxynucleotide-directed Mutagenesis"; Gene; 1983; vol. 26; pp. 101-106; Elsevier Science Publishers.

* cited by examiner

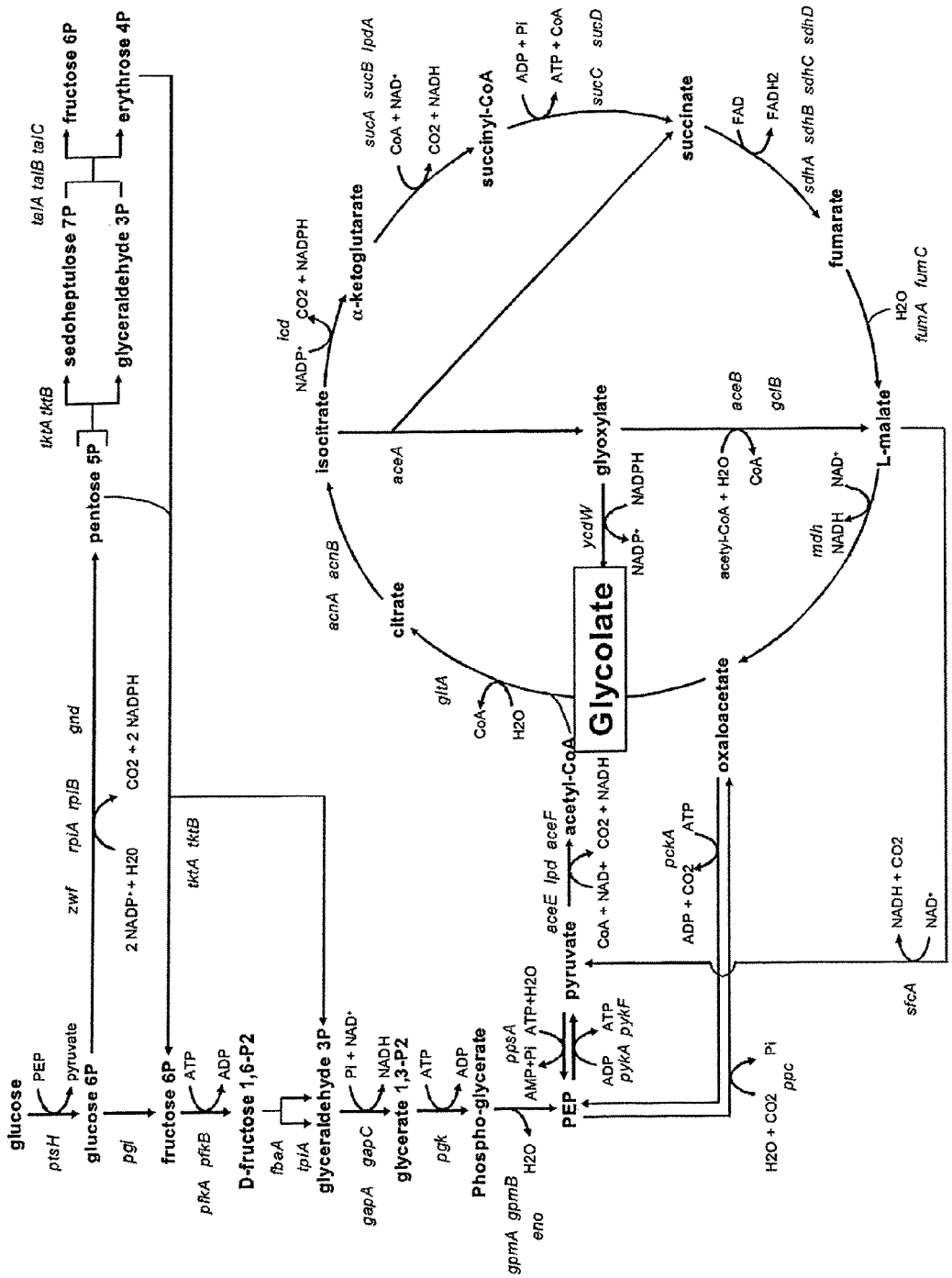

METHOD FOR PRODUCING GLYCOLIC ACID USING AN INDUCIBLE PROMOTER

CROSS REFERENCE TO RELATED APPLICATIONS

This application is a §371 National Stage Application of PCT/EP2011/059884, filed Jun. 15, 2011, which claims priority to European Application No. 10305635.4, filed Jun. 15, 2010 and U.S. Provisional Application No. 61/354,887, filed Jun. 15, 2010.

BACKGROUND OF THE INVENTION

1. Field of the Invention

The present invention relates to use of inducible promoters in the production of glycolic acid, by fermentation. The use of inducible promoters leads to a more stable glycolic acid producer strain.

2. Description of Related Art

Glycolic Acid ($HOCH_2COOH$), or glycolate, is the simplest member of the alpha-hydroxy acid family of carboxylic acids. Glycolic acid has dual functionality with both alcohol and moderately strong acid functional groups on a very small molecule. Its properties make it ideal for a broad spectrum of consumer and industrial applications, including use in water well rehabilitation, the leather industry, the oil and gas industry, the laundry and textile industry, and as a component in personal care products.

Glycolic Acid can also be used to produce a variety of polymeric materials, including thermoplastic resins comprising polyglycolic acid. Resins comprising polyglycolic acid have excellent gas barrier properties, and such thermoplastic resins comprising polyglycolic acid may be used to make packaging materials having the same properties (e.g., beverage containers, etc.). The polyester polymers gradually hydrolyze in aqueous environments at controllable rates. This property makes them useful in biomedical applications such as dissolvable sutures and in applications where a controlled release of acid is needed to reduce pH. Currently more than 15,000 tons of glycolic acid are consumed annually in the United states.

Although Glycolic Acid occurs naturally as a trace component in sugarcane, beets, grapes and fruit, it is mainly produced synthetically. Technologies to produce Glycolic Acid are described in the literature or in patent applications. For instance, Mitsui Chemicals, Inc. has described a method for producing the said hydroxycarboxylic acid from an aliphatic polyhydric alcohol having a hydroxyl group at the end by using a microorganism (EP 2 025 759 A1 and EP 2 025 760 A1). This method is a bioconversion as the one described by Michihiko Kataoka in its paper on the production of glycolic acid using ethylene glycol-oxidizing microorganisms (*Biosci. Biotechnol. Biochem.*, 2001).

Glycolic acid is also produced by bioconversion from glycolonitrile using mutant nitrilases with improved nitrilase activity as disclosed by Dupont de Nemours and Co in WO2006/069110 and U.S. Pat. No. 7,445,917. These documents teach a process using formaldehyde and hydrogen cyanide as precursors for the synthesis of glycolonitrile, and using an enzyme catalyst having nitrilase activity for the synthesis of glycolic acid from glycolonitrile. The main disadvantage of this process is that glycolonitrile is a chemical substance which may polymerize violently under the influence of traces of acid, or base, with fire or explosion hazard. This substance decomposes on heating producing toxic fumes including hydrogen cyanide and nitrogen oxides. Therefore it is listed as an extremely hazardous substance.

Methods for producing Glycolic Acid by fermentation from sugar, and in particular from renewable resources, using bacterial strains are disclosed in patent applications from Metabolic Explorer (WO 2007/141316 and WO 2010/108909).

The biological production of glycolic acid requires the formation of intermediates from the central metabolism of the bacterium (see FIG. 1.). Isocitrate situated at the junction of the Krebs cycle and the glyoxylate shunt is one of them (Tricarboxylic acid cycle and glyoxylate bypass, reviewed in Neidhardt, F. C. (Ed. in Chief), R. Curtiss III, J. L. Ingraham, E. C. C. Lin, K. B. Low, B. Magasanik. W. S. Reznikoff, M. Riley, M. Schaechter, and H. E. Umbarger (eds). 1996. *Escherichia coli* and *Salmonella:* Cellular and Molecular Biology. American Society for Microbiology). Isocitrate is either (1) cleaved into succinate and glyoxylate, a reaction catalyzed by isocitrate lyase, encoded, by the aceA gene or (2) converted into α-ketoglutarate by isocitrate dehydrogenase, encoded by the icd gene. Previous work described in patent application EP 2 027 277 has shown good productions of glycolic acid by strains having an attenuated expression of the icd gene. Reducing the flux in the TCA cycle to force it towards the glyoxylate shunt increased the yield of glycolic acid production significantly but at the same time, it weakened the strain.

The strains with an attenuated expression of the icd gene were not stable when grown for many generations, which is a strong disadvantage for industrial use. The authors found a solution to the problem by using inducible promoters.

Use of inducible promoters in biotechnological processes is in the art of industrial biotechnology. These promoters usually respond to chemical or physical stimuli exemplified by propionate (WO2007005837), zinc (WO2004020640), arabinose (WO1998011231), temperature ('Microbial conversion of glycerol to 1,3-propanediol by an engineered strain of *Escherichia coli.*' Tang X, Tan Y, Zhu H, Zhao K, Shen W. Appl Environ Microbiol. 2009 March; 75 (6): 1628-34.) and light.

Efficient glycolic acid production requires fine tuning of pathways. For maximum glycolic acid production and improved stability of producer strains, it can be beneficial to be able to modulate the expression of certain key enzymes during the process. For instance, the expression of the icd gene is absolutely required for biomass production but not for glycolic acid production and vice versa for aceA. Therefore, use of inducible promoters may be of interest in improving the overall yield of producing glycolic acid at an industrial level.

At this point use of inducible promoters to control expression of genes involved in glycolic acid production has never been considered nor reported.

The inventors have found that heterologous inducible promoters may be beneficial when used to regulate gene expression of genes involved in complex metabolic pathways such as glycolic acid biosynthesis.

SUMMARY

The present invention concerns a method for the production of glycolic acid in a fermentative process comprising the following steps:

culturing a modified microorganism in an appropriate culture medium comprising a source of carbon,
   modulating in said microorganism the expression of a target gene with an external stimulus, and recovering glycolic acid from the culture medium,
wherein in said modified microorganism, the expression of at least one gene involved in glycolic acid production is under the control of a heterologous inducible promoter whose activity is modulated with said external stimulus.

The invention also concerns the microorganism modified for glycolic acid production in which expression of at least one gene involved in glycolic acid biosynthesis is under the control of a heterologous inducible promoter.

BRIEF DESCRIPTION OF THE DRAWINGS

FIG. 1: Glycolic acid biosynthesis pathway.

DETAILED DESCRIPTION OF A PREFERRED EMBODIMENT

The present invention is related to a method for the production of glycolic acid in a fermentative process comprising the following steps:
 culturing a modified microorganism in an appropriate culture medium comprising a source of carbon,
 modulating in said microorganism the expression of a target gene with an external stimulus, and
 recovering glycolic acid from the culture medium,
wherein in said modified microorganism, the expression of at least one gene involved in glycolic acid production is under the control of a heterologous inducible promoter whose activity is modulated with said external stimulus.

The term "glycolic acid" or "gycolate" are used interchangeably and have the same meaning. They designate the molecule of formula $HOCH_2COOH$, that is the simplest member of the alpha-hydroxy acid family of carboxylic acids.

According to the invention, the terms "fermentative process', 'fermentation" or 'culture' are used interchangeably to denote the growth of bacteria on an appropriate growth medium.

The method for the production of glycolic acid in a fermentative process, is well known by the man skilled in the art. Different factors of the fermentative process can be modulated for the optimization of the process, such as the choice of the carbon source.

An "appropriate culture medium" is a medium appropriate for the culture and growth of the microorganism. Such media are well known in the art of fermentation of microorganisms, depending upon the microorganism to be cultured. The appropriate culture medium comprises a source of carbone. The term "source of carbon" refers to any carbon source capable of being metabolized by a microorganism wherein the substrate contains at least one carbon atom. The source of carbon is selected among the group consisting of glucose, sucrose, monosaccharides (such as fructose, mannose, xylose, arabinose), oligosaccharides (such as galactose, cellobiose . . . ), polysaccharides (such as cellulose), starch or its derivatives, glycerol and single-carbon substrates whereby glyoxylic acid is produced. An especially preferred carbon source is glucose. Another preferred carbon source is sucrose.

In a particular embodiment of the invention, the carbon source is derived from renewable feed-stock. Renewable feed-stock is defined as raw material required for certain industrial processes that can be regenerated within a brief delay and in sufficient amount to permit its transformation into the desired product.

The fermentation is generally conducted in fermenters with an appropriate culture medium adapted to the microorganism being used, containing at least one simple carbon source, and if necessary co-substrates for the production of metabolites (as described in patent application EP 09171297.6).

Those skilled in the art are able to define the culture conditions for the microorganisms according to the invention. In particular the bacteria are fermented at a temperature between 20° C. and 55° C., preferentially between 25° C. and 40° C., and more specifically about 30° C. to 37° C. for E. coli.

As an example of a known culture medium for E. coli, the culture medium can be of identical or similar composition to M9 medium (Anderson, 1946, Proc. Natl. Acad. Sci. USA 32:120-128), M63 medium (Miller, 1992; A Short Course in Bacterial Genetics: A Laboratory Manual and Handbook for Escherichia coli and Related Bacteria, Cold Spring-Harbor Laboratory Press, Cold Spring Harbor, N.Y.) or a medium such as defined by Schaefer et al. (1999, Anal. Biochem. 270: 88-96).

The term "microorganism" designates a bacterium, yeast or fungus. The bacterium is selected among gram positive bacteria or gram negative bacteria. Preferentially, the microorganism is selected among gram negative bacteria such as Enterobacteriaceae, or among gram positive bacteria such as Bacillaceae, Streptomycetaceae and Corynebacteriaceae. More preferentially, the microorganism is a species of Escherichia, Klebsiella, Pantoea, Salmonella or Corynebacterium. Even more preferentially, the microorganism is either the species Escherichia coli or Corynebacterium glutamicum. The term "modified microorganism" designates a genetically modified microorganism presenting an improved glycolic acid production. "Improved glycolic acid production" means that the amount of glycolic acid produced by the microorganism, and particularly the glycolic acid yield (ratio of glycolic acid produced per carbon source), is higher in the modified microorganism compared to the corresponding unmodified microorganism. The modified microorganism used in the method of the invention has two characteristics:
 it is modified for an improved glycolic acid production, and
 expression of at least one gene involved in glycolic acid production is under control, direct or indirect, of an inducible promoter.

The phrase "recovering glycolic acid from the culture medium" designates the action of recovering glycolic acid. Recovery of the glycolic acid is made by a step of concentration of glycolate in the bacteria or in the medium and isolation of glycolic acid from the fermentation broth and/or the biomass optionally remaining in portions or in the total amount (0-100%) in the end product from the fermentation culture. Optionally the process comprises a step of recovery of the glycolic acid produced in step (a) through a step of polymerization to at least glycolic acid dimers and (b) recovery of glycolic acid by depolymerisation from glycolic acid dimers, oligomers and/or polymers. According to a specific embodiment of the invention, the step of recovery comprises the recovering of derivatives and precursors of glycolic acid present in the culture medium.

The expression "modulating the expression of a target gene" means that the expression of a gene may be either allowed or repressed. This modulation may be achieved with an inducible promoter. Depending on the aim of this modulation, the man skilled in the art knows which kind of inducible system to use.

The term "inducible promoter" denotes a promoter whose activity can be increased or decreased upon an external stimulus. Stimuli can be physical or chemical in nature, such as temperature, light, chemicals etc.

Induction of the target gene can be obtained via direct or indirect transmission of the stimulus.

Indirect transmission can be accomplished by using heterologous RNA-polymerases that are under the control of an inducible promoter and that recognize specific promoters driving the expression of target genes involved in glycolic acid biosynthesis. In this case, the inducible promoter is not directly linked to the promoter of the target gene, but drives the expression of an RNA polymerase transcribing said promoter of the target gene.

These heterologous RNA polymerases can be e.g. T3 RNA polymerase, T7 RNA polymerase or other polymerase known to the expert in the field.

Direct transmission is accomplished when the expression of one target gene is under the control of an inducible promoter.

The phrase "under the control of a heterologous inducible promoter" designates the fact that the inducible promoter is not the native promoter of the gene and was introduced in a way to control, at least partially, the level of expression of the gene that is operably linked to it. The activity of an inducible promoter is induced by the presence or absence of biotic or abiotic factors. Expression of genes can be turned on or off, according to the needs of the man skilled in the art. These promoters might be chemically-regulated (in presence of tetracycline, hormones, etc) or physically-regulated, especially by heat or light. In a specific embodiment of the invention, the expression of at least one gene involved in glycolic acid production is under the direct control of an heterologous inducible promoter. This inducible promoter may be induced either by a physical stimulus or by a chemical stimulus.

In a first aspect of the invention, the external stimulus is chosen anion temperature or light, ie. the inducible promoter is a temperature-inducible promoter or a light-inducible promoter.

The inducible promoter is advantageously induced by temperature, and is selected among:
  promoters regulated by a modified repressor of phage lambda, such as:
    the promoter PR or a derivative of said promoterPR,
    the promoter PL or a derivative of said promoter PL,
  a modified lac promoter regulated by a temperature sensitive Lac repressor For these promoters, bibliographic references are the following:
  A genetic switch. Ptashne M. Blackwell Scientific, Cambridge, Mass. 1986;
  A genetic switch: Phage lambda revisited. Ptashne M. Cold Spring Harbor Lab Press. Cold Spring Harbor, N.Y. 2004;
  The bacteriophages, Part II: Life of phages, 8. Gene regulatory circuitry of phage λ, Little J. $2^{nd}$ edition 2004. Richard Calendared. Oxford University Press;
  Bukrinsky et al. *Gene*, 70 (1998) 415-417;
  Mandal & Lieb, 1976,
  Winstanley et al. 1989.

The repressor represses the expression from the cognate promoter by binding to specific binding sites in the promoter region thereby limiting the access of RNA polymerase to the promoter and reducing initiation or elongation of transcription.

According to an aspect of the invention, the modified, repressor of phage lambda is a temperature labile allele of the lambda repressor cI. Advantageously, said, repressor is the lambda repressor allele cI857 (On a thermosensitive repression system in the *Escherichia coli* lambda bacteriophage, Sussman R, Jacob F. C. R. Hebd. Seances Acad. Sci. 1962. 254, p1517). Sussman et al. report a new mutant of the bacteriophage, being in the lysogenic state when cultivated at 32° C., but wherein its lyse is induced when the culture is maintained at a temperature of 40° C. for one hour.

In a specific aspect of the invention, in the modified microorganism for the production of glycolic acid, the gene recA encoding the protein RecA has been deleted. The protein RecA is known to act as a protease on cI. Therefore the deletion of the gene encoding RecA excludes proteolysis of the lambda repressor cI.

The temperature-inducible promoter might advantageously be chosen between the promoter PR or a derivative, and the promoter PL or a derivative.

In another embodiment, the temperature-inducible promoter is a modified lac promoter regulated by a temperature sensitive Lac repressor.

In a second aspect of the invention, the external stimulus is a chemical stimulus, ie. the inducible promoter is chemically-regulated. In particular, the induction of the promoter's activity is linked to changes in the repression of carbon catabolite. Promoters that are activated by carbon catabolite repression are positively regulated via the activator "cAMP Repressor Protein" (CRP) at low concentrations of glucose or in the absence of glucose. In another embodiment of the invention, the inducible promoter is induced by the presence of specific carbon sources or of sugar alcohols. Examples of promoters that are induced by carbon sources or sugar alcohols include the arabinose or raffinose promoter and the mannitol promoter or glucitol promoters, respectively.

The principle of induction is based on the protein conformation. For a promoter activated by a specific stimulus (either physical or chemical stimuli), the cognate repressor is active under its native form. The presence of a specific stimulus induces a change of conformation of this repressor, which become unable to bind to the promoter and thus to activate gene transcription. Conversely for a promoter repressed by a specific stimulus, the cognate repressor is inactive under its native form and the presence of specific stimulus induces a change of its conformation which leads to an active form of the repressor which may repress gene transcription.

The man skilled in the art is able to choose an inducible promoter either activated or repressed by a physical or a chemical stimulus in accordance with the organism used, the culture conditions and the aim of modulation of the expression of a target gene.

According to a specific aspect, of the invention, the expression of genes of interest ('target gene') is regulated via "indirect transmission", i.e at least one gene involved in glycolic acid production is transcribed by a heterologous RNA polymerase whose expression is under the control of an inducible promoter.

In a specific embodiment of the invention, the heterologous RNA polymerase is chosen from T7, T3 polymerase.

According to the invention, the 'target gene' is at least one gene involved in glycolic acid production or in the production of its precursors. The target gene is under the control, direct or indirect, of a heterologous inducible promoter; as previously explained, either the gene is under the direct control of an inducible promoter, or the gene is transcribed by an inducible RNA polymerase or both combinations.

Genes involved in glycolic acid production in a microorganism are known in the art, and comprise genes involved in the glycolic acid specific biosynthesis pathway as well as genes involved in precursor-providing pathways and genes involved in glycolic acid consuming pathways.

Efficient production of glycolic acid requires the optimization of the glycolic acid specific pathway and several precursor-providing pathways. Glycolic acid producing strains have been described in patent applications EP 2 027 227 and WO 2010/108909, that are incorporated as reference into this application.

In particular, said glycolic acid producing strains comprise at least one of the following modifications:

Attenuation of the conversion of glyoxylate to products other than glycolate. (attenuation of aceB, glcB, gcl, eda)

unability to substantially metabolize glycolate (attenuation of glcDEFG, aldA)

increase of the glyoxylate pathway flux (attenuation of icd, aceK, pta, ackA, poxB, iclR or fadR, and/or overexpression of aceA)

increase of the conversion of glyoxylate to glycolate (overexpression of ycdW)

increase of the availability of NADPH (attenuation of pgi, udhA, edd).

Said glycolic acid producing strains may comprise furthermore at least one of the following modifications:

attenuation of the genes ldhA and mgsA attenuation of the gene arcA attenuation of at least one of the genes glcA, lldP, and yjcG.

According to the present invention, to increase glycolic acid production in a strain already modified for glycolic acid production, at least one of the following genes involved in glycolic acid production may be under the control of an inducible promoter whose activity is modulated with an external stimulus:

a) Genes encoding the enzymes involved in the crossroad of the TCA cycle and the glyoxylate shunt:

| gene | geneID | function |
| --- | --- | --- |
| icd | b1136 | isocitrate dehydrogenase |
| aceA | b4015 | isocitrate lyase | b) Genes encoding the enzyme directly involved in the glycolic acid biosynthesis:

| ghrA/ycdW | b1033 | NADPH-glyoxylate reductase |
| --- | --- | --- | c) Genes encoding enzymes directly or indirectly involved in the production of cofactor NADPH and regulation of the redox state of the cell:

| pntAB | b1602 and b1603 | pyridine nucleotide transhydrogenase |
| --- | --- | --- |
| udhA | b3962 | pyridine nucleotide transhydrogenase, soluble |
| pgi | b4025 | glucose-6-phosphate isomerase |
| arcA | b4401 | aerobic respiration control protein | d) Genes involved in anplerotic pathways:

| maeA | b1479 | NAD-dependent malate dehydrogenase |
| --- | --- | --- |
| maeB | b2463 | NADP-dependent malic enzyme |
| mdh | b3236 | Malate dehydrogenase |
| pck | b3403 | Phosphoenolpyruvate (PEP) carboxykinase |
| ppc | b3956 | Phosphoenolpyruvate carboxylase | e) Genes encoding enzymes involved in acetate metabolism:

| ackA | b2296 | acetate kinase activity |
| --- | --- | --- |
| pta | b2297 | Phosphate acetyltransferase |
| poxB | b0871 | Pyruvate oxidase |
| acs | b4069 | Acetyl-coenzyme A synthetase | f) Genes encoding enzymes involved in the transport of glycolate through the membrane:

| lldP | b3603 | probable lactate/proton symporter |
| --- | --- | --- |
| glcA | b2975 | glycolate transporter |
| yjcG/actP | b4067 | acetate/glycolate permease | g) Genes encoding enzymes involved in the production of the lactate as byproduct:

| ldhA | b1380 | Lactate dehydrogenase |
| --- | --- | --- |
| mgsA | b0963 | Methylglyoxal synthase |

According to the invention, at least two genes of the preceding genes mentioned and any combination of these genes are under the control of inducible promoters to increase glycolic acid production.

In a preferred embodiment of the invention, the expression of the gene icd is under the control of a heterologous inducible promoter, directly or indirectly.

The enzyme isocitrate dehydrogenase belongs to the TCA cycle and catalyzes the transformation of isocitrate to α-ketoglutarate. Since isocitrate is at the junction of the TCA cycle which leads to biomass and the glyoxylic shunt which leads to glycolic acid, its distribution in these pathways has a huge impact on the production of glycolic acid.

In a specific embodiment, the gene icd is under the control of an inducible promoter, which allows expression of icd gene at 37° C. to 42° C. and represses expression of icd gene at 28° C. to 32° C.

In a preferred embodiment of the invention, the modified microorganism is grown from 37° C. to 42° C. to produce biomass (conditions wherein icd is expressed) and from 28° C. to 30° C. to produce glycolic acid (conditions wherein icd is repressed).

In a specific embodiment of the invention, the step of recovery of the produced glycolic acid in the culture medium comprises the recovering of derivatives and precursors of glycolic acid present in the culture medium. "Derivatives or precursors" of glycolic acid designates all intermediate compounds in the metabolic pathway of formation and degradation of glycolic acid. Precursors of glycolic acid are in particular: citrate, isocitrate, glyoxylate, and in general all compounds of the glyoxylate cycle. Derivatives of glycolic acid are in particular glycolate esters such as ethyl glycolate ester, methyl glycolate ester and polymers containing glycolate such as polyglycolic acid.

Genes controlled, by the inducible promoter may either be at its native position on the chromosome or integrated at a non-native position. One or several integrations of the gene controlled by the inducible promoter may be required for optimal glycolic acid production. Similarly, one or several copies of the regulator gene may be required for optimal expression. Different ratios of repressor gene copies and promoters may be used, to fine-tune expression.

The gene under the control of the inducible promoter should, preferentially be integrated into loci, whose modification does not have a negative impact on glycolic acid production. Examples for loci into which the gene may be integrated are:

| Locus | Accession Number | Function |
|---|---|---|
| aaaD | 87081759 | Pseudogene, phage terminase protein A homolog, N-terminal fragment |
| aaaE | 1787395 | Pseudogene, phage terminase protein A homolog, C-terminal fragment |
| afuB | 1786458 | Pseudogene, ferric ABC family transporter permease; C-terminal fragment |
| afuC | 87081709 | predicted ferric ABC transporter subunit (ATP-binding component) |
| agaA | 48994927 | Pseudogene, C-terminal fragment, GalNAc-6-P deacetylase |
| agaW | 1789522 | Pseudogene, N-terminal fragment, PTS system EIICGalNAc |
| alpA | 1788977 | protease |
| appY | 1786776 | DNA-binding transcriptional activator |
| argF | 1786469 | ornithine carbamoyltransferase |
| argU | none | arginine tRNA |
| argW | none | Arginine tRNA(CCU) 5 |
| arpB | 87081959 | Pseudogene reconstruction, ankyrin repeats |
| arrD | 1786768 | lysozyme |
| arrQ | 1787836 | Phage lambda lysozyme R protein homolog |
| arsB | 87082277 | arsenite transporter |
| arsC | 1789918 | arsenate reductase |
| arsR | 1789916 | DNA-binding transcriptional repressor |
| beeE | 1787397 | Pseudogene, N-terminal fragment, portal protein |
| borD | 1786770 | bacteriophage lambda Bor protein homolog |
| cohE | 1787391 | CI-like repressor |
| croE | 87081841 | Cro-like repressor |
| cspB | 1787839 | Cold shock protein |
| cspF | 1787840 | Cold shock protein homolog |
| cspI | 1787834 | Cold shock protein |
| cybC | 1790684 | Pseudogene, N-terminal fragment, cytochrome b562 |
| dicA | 1787853 | Regulatory for dicB |
| dicB | 1787857 | Control of cell division |
| dicC | 1787852 | Regulatory for dicB |
| dicF | none | DicF antisense sRNA |
| eaeH | 1786488 | Pseudogene, intimin homolog |
| efeU | 87081821 | Pseudogene reconstruction, ferrous iron permease |
| emrE | 1786755 | multidrug resistance pump |
| essD | 1786767 | predicted phage lysis protein |
| essQ | 87081934 | Phage lambda S lysis protein homolog |
| exoD | 1786750 | Pseudogene, C-terminal exonuclease fragment |
| eyeA | none | novel sRNA, unknown function |
| Flu | 48994897 | Antigen 43 |
| flxA | 1787849 | unknown |
| gapC | 87081902 | Pseudogene reconstruction, GAP dehydrogenase |
| gatR | 87082039 | Pseudogene reconstruction, repressor for gat operon |
| glvC | 1790116 | Pseudogene reconstruction |
| glvG | 1790115 | Pseudogene reconstruction, 6-phospho-beta-glucosidase |
| gnsB | 87081932 | Multicopy suppressor of secG(Cs) arid fabA6(Ts) |
| gtrA | 1788691 | Bactoprenol-linked glucose translocase |
| gtrB | 1788692 | Bactoprenol glucosyl transferase |
| gtrS | 1788693 | glucosyl transferase |
| hokD | 1787845 | Small toxic membrane polypeptide |
| Icd | 1787381 | Isocitrate dehydrogenase |
| icdC | 87081844 | pseudogene |
| ilvG | 87082328 | Pseudogene reconstruction, acetohydroxy acid synthase II |
| insA | 1786204 | IS1 gene, transposition function |
| insA | 1786204 | IS1 gene, transposition function |
| insB | 1786203 | IS1 insertion sequence transposase |
| insB | 1786203 | IS1 insertion sequence transposase |
| insC | 1786557 | IS2 gene, transposition function |
| insD | 1786558 | IS2 gene, transposition function |
| insD | 1786558 | IS2 gene, transposition function |
| insE | 1786489 | IS3 gene, transposition function |
| insF | 1786490 | IS3 gene, transposition function |
| insH | 1786453 | IS5 gene, transposition function |
| insH | 1786453 | IS5 gene, transposition function |
| insH | 1786453 | IS5 gene, transposition function |
| insI | 1786450 | IS30 gene, transposition function |
| insI(−1) | 1786450 | IS30 gene, transposition function |
| insM | 87082409 | Pseudogene, truncated IS600 transposase |
| insN | 1786449 | Pseudogene reconstruction, IS911 transposase ORFAB |
| insO | none | Pseudogene reconstruction, IS911 transposase ORFAB |
| insX | 87081710 | Pseudogene IS3 family transposase, N-terminal fragment |
| insZ | 1787491 | Pseudogene reconstruction, IS4 transposase family, in ISZ' |
| intA | 1788974 | Integrase gene |
| intB | 1790722 | Pseudogene reconstruction, P4-like integrase |
| intD | 1786748 | predicted integrase |
| intE | 1787386 | e14 integrase |
| intF | 2367104 | predicted phage integrase |
| intG | 1788246 | Pseudogene, integrase homolog |
| intK | 1787850 | Pseudogene, integrase fragment |
| intQ | 1787861 | Pseudogene, integrase fragment |
| intR | 1787607 | Integrase gene |

-continued

| Locus | Accession Number | Function |
|---|---|---|
| intS | 1788690 | Integrase |
| intZ | 1788783 | Putative integrase gene |
| isrC | none | Novel sRNA, function unknown |
| jayE | 87081842 | Pseudogene, C-terminal fragment, baseplate |
| kilR | 87081884 | Killing function of the Rac prophage |
| lafU | none | Pseudogene, lateral flagellar motor protein fragment |
| lfhA | 87081703 | Pseudogene, lateral flagellar assembly protein fragment |
| lit | 1787385 | Cell death peptidase |
| lomR | 1787632 | Pseudogene reconstruction, lom homolog; outer membrane protein interrupted by IS5Y, missing N-terminus |
| malS | 1789995 | α-amylase |
| mcrA | 1787406 | 5-methylcytosine-specific DNA binding protein |
| mdtQ | 87082057 | Pseudogene reconstruction, lipoprotein drug pump OMF family |
| melB | 1790561 | melibiose permease |
| mmuM | 1786456 | homocysteine methyltransferase |
| mmuP | 870811708 | S-methylglycolic acid permease |
| mokA | none | Pseudogene, overlapping regulatory peptide, enables hokB |
| ninE | 1786760 | unknown |
| nmpC | 1786765 | Pseudogene reconstruction, OM porin, interrupted by IS5B |
| nohD | 1786773 | DNA packaging protein |
| nohQ | 1787830 | Pseudogene, phage lambda Nu1 homolog, terminase small subunit family, putative DNA packaging protein |
| ogrK | 1788398 | Positive regulator of P2 growth |
| ompT | 1786777 | outer membrane protease VII |
| oweE | none | Pseudogene, lambda replication protein O homolog |
| oweS | 1788700 | Pseudogene, lambda replication protein O homolog |
| pauD | none | argU pseudogene, DLP12 prophage attachment site |
| pawZ | none | CPS-53 prophage attachment site attR, argW pseudogene |
| pbl | 87082169 | Pseudogene reconstruction, pilT homolog |
| peaD | 87081754 | Pseudogene, phage lambda replication protein P family; C-tertninal fragment |
| perR | 1786448 | predicted DNA-binding transcriptional regulator |
| pgaA | 1787261 | outer membrane porin of poly-β-1,6-N-acetyl-D-glucosamine (PGA) biosynthesis pathway |
| pgaB | 1787260 | PGA N-deacetylase |
| pgaC | 1787259 | UDP-N-acetyl-D-glucosamine β-1,6-N-acetyl-D-glucosaminyl transferase |
| pgaD | 1787258 | predicted inner membrane protein |
| phnE | 87082370 | Pseudogene reconstruction, phosphonate permease |
| pinE | 1787404 | DNA invertase |
| pinH | 1789002 | Pseudogene, DNA invertase, site-specific recombination |
| pinQ | 1787827 | DNA invertase |
| pinR | 1787638 | DNA invertase |
| prfH | 1786431 | Pseudogene, protein release factor homolog |
| psaA | none | ssrA pseudogene, CP4-57 attachment site duplication |
| ptwF | none | thrW pseudogene, CP4-6 prophage attachment site |
| quuD | 1786763 | predicted antitermination protein |
| quuQ | 87081935 | Lambda Q antitermination protein homolog |
| racC | 1787614 | unknown |
| racR | 1787619 | Rac prophage repressor, cI-like |
| ralR | 1787610 | Restriction alleviation gene |
| rbsA | 1790190 | D-ribose ABC transporter subunit (ATP-binding component) |
| rbsD | 87082327 | D-ribose pyranase |
| recE | 1787612 | RecET recombinase |
| recT | 1787611 | RecET recombinase |
| relB | 1787847 | Antitoxin for RelE |
| relE | 1787846 | Sequence-specific mRNA endoribonuclease |
| Rem | 1787844 | unknown |
| renD | 87081755 | Pseudogene reconstruction, lambda ren homolog, interrupted by IS3C; putative activator of lit transcription |
| rhsE | 1787728 | Pseudogene, rhs family, encoded within RhsE repeat |
| rnlA | 1788983 | RNase LS, endoribonuclease |
| Rph | 1790074 | Pseudogene reconstruction, RNase PH |
| rusA | 1786762 | Endonuclease |
| rzoD | 87081757 | Probable Rz1-like lipoprotein |
| rzoQ | none | Probable Rz1-like lipoprotein |
| rzoR | 87081890 | Probable Rz1-like lipoprotein |
| rzpD | 1786769 | predicted murein endopeptidase |
| rzpQ | 1787835 | Rz-like equivalent |
| rzpR | 87081889 | Pseudogene, Rz homolog |
| sieB | 87081885 | Superinfection exclusion protein |
| sokA | none | Pseudogene, antisense sRNA blocking mokA/hokA translation |
| stfE | 87081843 | C-terminal Stf variable cassette, alternate virion-host specificity protein; Tail Collar domain, pseudogene |
| stfP | 1787400 | Predicted tail fiber protein |
| stfR | 87081892 | Side-tail fiber protein |
| tfaD | 87081759 | Pseudogene, tail fiber assembly gene, C-terminal fragment |
| tfaE | 1787402 | Predicted tail fiber assembly gene |

-continued

| Locus | Accession Number | Function |
|---|---|---|
| tfaP | 1787401 | Predicted tail fiber assembly gene |
| tfaQ | 2367120 | Phage lambda tail fiber assembly gene homolog |
| tfaR | 1787637 | Phage lambda tail fiber assembly gene homolog |
| tfaS | 87082088 | Pseudogene, tail fiber assembly gene, C-terminal fragment |
| tfaX | 2367110 | Pseudogene reconstruction, tail fiber assembly gene, C-terminal fragment |
| thrW | none | threonine tRNA (attachment site of the CP4-6 prophage) |
| torI | 87082092 | CPS-53/KpLE1 exisionase |
| treB | 2367362 | subunit of trehalose PTS permease (IIB/IIC domains) |
| treC | 1790687 | trehalose-6-phosphate hydrolase |
| trkG | 1787626 | Major constitutive K+ uptake permease |
| ttcA | 1787607 | Integrase gene |
| ttcC | none | Pseudogene, prophage Rac integration site ttcA duplication |
| uidB | 1787902 | Glucuronide permease, inactive point mutant |
| uxaA | 1789475 | altronate hydrolase |
| uxaC | 2367192 | uronate isomerase |
| wbbL | 1788343 | Pseudogene reconstruction, rhamnosyl transferase |
| wcaM | 1788356 | predicted colanic acid biosynthesis protein |
| xisD | none | Pseudogene, exisionase fragment in defective prophage DLP12 |
| xisE | 1787387 | e14 excisionase |
| yabP | 1786242 | Pseudogene reconstruction |
| yafF | 87081701 | Pseudogene, C-terminal fragment, H repeat-associated protein |
| yafU | 1786411 | Pseudogene, C-terminal fragment |
| yafW | 1786440 | antitoxin of the YkfI-YafW toxin-antitoxin system |
| yafX | 1786442 | unknown |
| yafY | 1786445 | predicted DNA-binding transcriptional regulator; inner membrane lipoprotein |
| yafZ | 87081705 | unknown |
| yagA | 1786462 | predicted DNA-binding transcriptional regulator |
| yagB | 87081711 | Pseudogene, antitoxin-related, N-terminal fragment |
| yagE | 1786463 | predicted lyase/synthase |
| yagF | 1786464 | predicted dehydratase |
| yagG | 1786466 | putative sugar symporter |
| yagH | 1786467 | putative β-xylosidase |
| yagI | 1786468 | predicted DNA-binding transcriptional regulator |
| yagJ | 1786472 | unknown |
| yagK | 1786473 | unknown |
| yagL | 1786474 | DNA-binding protein |
| yagM | 2367101 | unknown |
| yagN | 2367102 | unknown |
| yagP | 1786476 | Pseudogene, LysR family, fragment |
| yaiT | 1786569 | Pseudogene reconstruction, autotransporter family |
| yaiX | 87082443 | Pseudogene reconstruction, interrupted by IS2A |
| ybbD | 1786709 | Pseudogene reconstruction, novel conserved family |
| ybcK | 1786756 | predicted recombinase |
| ybcL | 1786757 | predicted kinase inhibitor |
| ybcM | 1786758 | predicted DNA-binding transcriptional regulator |
| ybcN | 1786759 | DNA base-flipping protein |
| ybcO | 1786761 | unknown |
| ybcV | 87081758 | unknown |
| ybcW | 1786772 | unknown |
| ybcY | 48994878 | Pseudogene reconstruction, methyltransferase family |
| ybeM | 1786843 | Pseudogene reconstruction, putative CN hydrolase |
| ybfG | 87081771 | Pseudogene reconstruction, novel conserved family |
| ybfI | none | Pseudogene reconstruction, KdpE homolog |
| ybfL | 87081775 | Pseudogene reconstruction, H repeat-associated protein |
| ybfO | 1786921 | Pseudogene, copy of Rhs core with unique extension |
| ycgH | 87081847 | Pseudogene reconstruction |
| ycgI | 1787421 | Pseudogene reconstruction, autotransporter homolog |
| ycjV | 1787577 | Pseudogene reconstruction, malK paralog |
| ydaC | 1787609 | unknown |
| ydaE | 87081883 | Metallothionein |
| ydaF | 87081886 | unknown |
| ydaG | 87081887 | unknown |
| ydaQ | 87081882 | Putative exisionase |
| ydaS | 1787620 | unknown |
| ydaT | 1787621 | unknown |
| ydaU | 1787622 | unknown |
| ydaV | 1787623 | unknown |
| ydaW | 87081888 | Pseudogene, N-terminal fragment |
| ydaY | 1787629 | pseudogene |
| ydbA | 87081898 | Pseudogene reconstruction, autotransporter homolog |
| yddK | 1787745 | Pseudogene, C-terminal fragment, leucine-rich |
| yddL | 1787746 | Pseudogene, OmpCFN porin family, N-terminal fragment |
| ydeT | 1787782 | Pseudogene, FimD family, C-terminal fragment |
| ydfA | 1787854 | unknown |
| ydfB | 87081937 | unknown |
| ydfC | 1787856 | unknown |

-continued

| Locus | Accession Number | Function |
| --- | --- | --- |
| ydfD | 1787858 | unknown |
| ydfE | 1787859 | Pseudogene, N-terminal fragment |
| ydfJ | 1787824 | Pseudogene reconstruction, MFS family |
| ydfK | 1787826 | Cold shock gene |
| ydfO | 87081931 | unknown |
| ydfR | 1787837 | unknown |
| ydfU | 87081936 | unknown |
| ydfV | 1787848 | unknown |
| ydfX | 1787851 | pseudogene |
| yedN | 87082002 | Pseudogene reconstruction, IpaH/YopM family |
| yedS | 87082009 | Pseudogene reconstruction, outer membrane protein homolog |
| yeeH | none | Pseudogene, internal fragment |
| yeeL | 87082016 | Pseudogene reconstruction, glycosyltransferase family |
| yeeP | 87082019 | Pseudogene, putative GTP-binding protein |
| yeeR | 87082020 | unknown |
| yeeS | 1788312 | unknown |
| yeeT | 1788313 | unknown |
| yeeU | 1788314 | Antitoxin component of toxin-antitoxin protein pair YeeY-YeeU |
| yeeV | 1788315 | Toxin component of toxin-antitoxin protein pair YeeV-YeeU |
| yeeW | 1788316 | pseudogene |
| yegZ | none | Pseudogene, gpD phage P2-like protein D; C-terminal fragment |
| yehH | 87082046 | Pseudogene reconstruction |
| yehQ | 87082050 | Pseudogene reconstruction |
| yejO | 1788516 | Pseudogene reconstruction, autotransporter homolog |
| yfaH | 1788571 | Pseudogene reconstruction, C-terminal fragment, LysR homolog |
| yfaS | 87082066 | Pseudogene reconstruction |
| yfcU | 1788678 | Pseudogene reconstruction, FimD family |
| yfdK | 1788696 | unknown |
| yfdL | 1788697 | Pseudogene, tail fiber protein |
| yfdM | 87082089 | Pseudogene, intact gene encodes a predicted DNA adenine methyltransferase |
| yfdN | 1788699 | unknown |
| yfdP | 1788701 | unknown |
| yfdQ | 1788702 | unknown |
| yfdR | 87082090 | unknown |
| yfdS | 1788704 | unknown |
| yfdT | 1788705 | unknown |
| yffL | 1788784 | unknown |
| yffM | 1788785 | unknown |
| yffN | 1788786 | unknown |
| yffO | 1788787 | unknown |
| yffP | 1788788 | unknown |
| yffQ | 1788790 | unknown |
| yffR | 1788791 | unknown |
| yffS | 1788792 | unknown |
| yfjH | 1788976 | unknown |
| yfjI | 1788978 | unknown |
| yfjJ | 1788979 | unknown |
| yfjK | 1788980 | unknown |
| yfjL | 1788981 | unknown |
| yfjM | 1788982 | unknown |
| yfjO | 87082140 | unknown |
| yfjP | 48994902 | unknown |
| yfjQ | 1788987 | unknown |
| yfjR | 1788988 | unknown |
| yfjS | 87082142 | unknown |
| yfjT | 1788990 | unknown |
| yfjU | 1788991 | pseudogene |
| yfjV | 1788992 | Pseudogene reconstruction, arsB-like C-terminal fragment |
| yfjW | 2367146 | unknown |
| yfjX | 1788996 | unknown |
| yfjY | 1788997 | unknown |
| yfjZ | 1788998 | Antitoxin component of putative toxin-antitoxin YpjF-YfjZ |
| ygaQ | 1789007 | Pseudogene reconstruction, has alpha-amylase-related domain |
| ygaY | 1789035 | Pseudogene reconstruction, MFS family |
| ygeF | 2367169 | Pseudogene reconstruction, part of T3SS PAI ETT2 remnant |
| ygeK | 87082170 | Pseudogene reconstruction, part of T3SS PAI ETT2 remnant |
| ygeN | 1789221 | Pseudogene reconstruction, orgB homolog |
| ygeO | 1789223 | Pseudogene, orgA homolog, part of T3SS PAI ETT2 remnant |
| ygeQ | 1789226 | Pseudogene reconstruction, part of T3SS PAI ETT2 remnant |
| yghE | 1789340 | Pseudogene reconstruction, general secretion protein family |
| yghF | 1789341 | Pseudogene, general secretion protein |
| yghO | 1789354 | Pseudogene, C-terminal fragment |
| yghX | 1789373 | Pseudogene reconstruction, S9 peptidase family |
| yhcE | 1789611 | Pseudogene reconstruction, interrupted by IS5R |
| yhdW | 1789668 | Pseudogene reconstruction |
| yhiL | 87082275 | Pseudogene reconstruction, FliA regulated |

-continued

| Locus | Accession Number | Function |
|---|---|---|
| yhiS | 1789920 | Pseudogene reconstruction, interrupted by IS5T |
| yhjQ | 1789955 | Pseudogene reconstruction |
| yibJ | 48994952 | Pseudogene reconstruction, Rhs family |
| yibS | none | Pseudogene reconstruction, Rhs family, C-terminal fragment |
| yibU | none | Pseudogene reconstruction, H repeat-associated protein |
| yibW | none | Pseudogene reconstruction, rhsA-linked |
| yicT | none | Pseudogene, N-terminal fragment |
| yifN | 2367279 | Pseudogene reconstruction |
| yjbI | 1790471 | Pseudogene reconstruction |
| yjdQ | none | Pseudogene reconstruction, P4-like integrase remnant |
| yjgX | 1790726 | Pseudogene reconstruction, EptAB family |
| yjhD | 87082406 | Pseudogene, C-terminal fragment |
| yjhE | 87082407 | Pseudogene, putative transporter remnant |
| yjhR | 1790762 | Pseudogene reconstruction, helicase family, C-terminal fragment |
| yjhV | 1790738 | Pseudogene, C-terminal fragment |
| yjhY | none | Pseudogene reconstruction, novel zinc finger family |
| yjhZ | none | Pseudogene reconstruction, rimK paralog, C-terminal fragment |
| yjiP | 1790795 | Pseudogene reconstruction, transposase family |
| yjiT | 87082428 | Pseudogene, N-terminal fragment |
| yjiV | none | Pseudogene reconstruction, helicase-like, C-terminal fragment |
| yjjN | 87082432 | predicted oxidoreductase |
| ykfA | 87081706 | putative GTP-binding protein |
| ykfB | 1786444 | unknown |
| ykfC | 87081707 | Pseudogene, retron-type reverse transcriptase family, N-terminal fragment |
| ykfF | 1786443 | unknown |
| ykfG | 2367100 | unknown |
| ykfH | 87081704 | unknown |
| ykfI | 1786439 | toxin of the YkfI-YafW toxin-antitoxin system |
| ykfJ | 1786430 | Pseudogene, N-terminal fragment |
| ykfK | 1786445 | Pseudogene, N-terminal fragment |
| ykfL | none | Pseudogene, C-terminal fragment |
| ykfN | none | Pseudogene, N-terminal remnant, YdiA family |
| ykgA | 87081714 | Pseudogene, N-terminal fragment, AraC family |
| ykgP | none | Pseudogene, oxidoreductase fragment |
| ykgQ | none | Pseudogene, C-terminal fragment of a putative dehydrogenase |
| ykgS | none | Pseudogene internal fragment |
| ykiA | 1780591 | Pseudogene reconstruction, C-terminal fragment |
| ylbE | 1786730 | Pseudogene reconstruction, yahG paralog |
| ylbG | 87081748 | Pseudogene reconstruction, discontinuous N-terminal fragment |
| ylbH | 1756708 | Pseudogene, copy of Rhs core with unique extension |
| ylbI | none | Pseudogene, internal fragment, Rhs family |
| ylcG | 87081756 | unknown |
| ylcH | none | unknown |
| ylcI | none | unknown |
| ymdE | 87081823 | Pseudogene, C-terminal fragment |
| ymfD | 1787383 | Putative SAM-dependent methyltransferase |
| ymfE | 1787384 | unknown |
| ymfI | 87081839 | unknown |
| ymfJ | 87081840 | unknown |
| ymfL | 1787393 | unknown |
| ymfM | 1787394 | unknown |
| ymfQ | 1787399 | Putative baseplate or tail fiber proteintt |
| ymfR | 1787396 | unknown |
| ymjC | none | Pseudogene, N-terminal fragment |
| ymjD | none | Expressed deletion pseudogene fusion remnant protein |
| ynaA | 1787631 | Pseudogene, N-terminal fragment |
| ynaE | 1787639 | Cold shock gene |
| ynaK | 1787628 | unknown |
| yncI | 1787731 | Pseudogene reconstruction, H repeat-associated, RhsE-linked |
| yncK | none | Pseudogene reconstruction, transposase homolog |
| yneL | 1787784 | Pseudogene reconstruction, C-terminal fragment, AraC family |
| yneO | 1787788 | Pseudogene reconstruction, putative OM autotransporter adhesi |
| ynfN | 87081933 | Cold shock gene |
| ynfO | none | unknown |
| yoeA | 87082018 | Pseudogene reconstruction, interrupted by IS2F |
| yoeD | none | Pseudogene, C-terminal fragment of a putative transposase |
| yoeF | 87082021 | Pseudogene, C-terminal fragment |
| yoeG | none | pseudogene, N-terminal fragment |
| yoeH | none | pseudogene, C-terminal fragment |
| ypdJ | 87082091 | Pseudogene, exisonase fragment |
| ypjC | 1789003 | Pseudogene reconstruction |
| ypjF | 1788999 | Toxin component of putative toxin-antitoxin pair YpjF-YfjZ |
| ypjI | none | Pseudogene reconstruction |
| ypjJ | 87082144 | unknown |
| ypjK | 87082141 | unknown |
| yqfE | 1789281 | Pseudogene reconstruction, C-terminal fragment, LysR family |

-continued

| Locus | Accession Number | Function |
| --- | --- | --- |
| yqiG | 48994919 | Pseudogene reconstruction, FimD family, interrupted by IS2I |
| yrdE | none | Pseudogene reconstruction, C-terminal fragment, yedZ paralog |
| yrdF | none | Pseudogene, N-terminal fragment |
| yrhA | 87082266 | Pseudogene reconstruction, interrupted by IS1E |
| yrhC | 87082273 | Pseudogene reconstruction, N-terminal fragment |
| ysaC | none | Pseudogene, C-terminal remnant |
| ysaD | none | Pseudogene, internal sequence remnant |
| ytfA | 1790650 | Pseudogene, C-terminal fragment |
| yzgL | 87082264 | Pseudogene, putative periplasmic solute binding protein |

The invention is also related to a microorganism modified for an improved production of glycolic acid wherein the expression of at least one gene involved in glycolic acid production is under the control, direct or indirect, of a heterologous inducible promoter as defined above.

Several modifications were previously introduced into said microorganism, and in particular modifications allowing the following metabolic changes:
i) the microorganism cannot metabolize glyoxylate to other compounds than glycolate, by inactivating the genes coding for the malate synthases (aceB and glcB), the glyoxylate carboligase (gcl) and the 2-keto-3-deoxy-gluconate 6-phosphate aldolase (eda),
ii) the microorganism cannot metabolize glycolate, by attenuating genes glcDEF and aldA,
iii) the glyoxylate pathway flux is increased by attenuation of icd, acek, pta, ack, poxB, iclR or fadR and/or by overexpression of aceA,
iv) the conversion of glyoxylate to glycolate is increased by overexpressing endogenous encoding genes like ycdW,
v) the availability of NADPH is increased by attenuating the expression of genes pgi, udhA and edd.

Modifications were described in patent applications EP 2 027 227 and WO 2010/108909, hereby incorporated by reference.

In the description of the present invention, genes and proteins are identified using the denominations of the corresponding genes in *E. coli*. However, and unless specified otherwise, use of these denominations has a more general meaning according to the invention and covers all the corresponding genes and proteins in other organisms, more particularly microorganisms.

Using the references given in GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism. These routine methods of molecular biology are well known to those skilled in the art, and are claimed, for example, in Sambrook et al. (1989 Molecular Cloning: a Laboratory Manual. $2^{nd}$ ed. Cold. Spring Harbor Lab., Cold Spring Harbor, N.Y.)

PFAM (protein families database of alignments and hidden Markov models; http://www.sanger.ac.uk/Software/Pfam/) represents a large collection of protein sequence alignments. Each PFAM makes it possible to visualize multiple alignments, see protein domains, evaluate distribution among organisms, gain access to other databases, and visualize known protein structures.

COGs (clusters of orthologous groups of proteins; http://www.ncbi.nlm.nih.gov/COG/ are obtained by comparing protein sequences from fully sequenced genomes representing major phylogenic lines. Each COG is defined from at least three lines, which permits the identification of former conserved domains.

The means of identifying homologous sequences and their percentage homologies are well known to those skilled in the art, and include in particular the BLAST programs, which can be used from the website http://www.ncbi.nlm.nih.gov/BLAST/ with the default parameters indicated on that website. The sequences obtained can then be exploited (e.g., aligned) using, for example, the programs CLUSTALW (http://www.ebi.ac.uk/clustalw/) or MULTALIN (http://bio-info.genotoul.fr/multalin/multalin.html), with the default parameters indicated on those websites.

In a specific aspect of the invention the microorganism previously genetically modified to produce glycolic acid contains at least one gene, which expression is under control of a heterologous inducible promoter, selected among icd, aceA, ycdW, pgi, pntAB, udhA.arcA, maeA, maeB, mdh, pck, ppc, ackA, pta, poxB, lldP, glcA, yjcG, IdhA and mgsA. More preferably the gene under control of a heterologous inducible promoter is icd.

In a preferred aspect of the invention, in the modified microorganism, the use of the inducible promoter allows expression of the icd gene at 37° C. to 42° C. and represses expression of the icd gene at 28° C. to 32° C.

In another embodiment of the invention, the microorganism presents a glycolic acid production of at least 50% of the initial production after 30 generations, preferentially of at least 70% of the initial production after 30 generations, most preferably 90% of the initial production after 30 generations.

Said microorganism presents a much more stable production of glycolic acid during a fermentation culture for several generations at an industrial scale.

The man skilled in the art is able to determine the number of generations for a specific microorganism in a fermentation process. A population of bacteria double every generation. To determine the number of cell in a culture, the man skilled in the art uses for *E. coli* the following formula; 0.4 OD unit=$2.10^8$ cells/mL (OD unit means Optical Density unit or Absorbance).

Generic Protocols Used to Build the Strains Producing Glycolic Acid Described in the Following Examples Protocol 1: Introduction of a PCR Product, for Recombination and Selection of the Recombinants (FRT System)

The oligonucleotides chosen and given in Table 1 for replacement of a gene or an intergenic region were used, to amplify either the chloramphenicol resistance cassette from the plasmid pKD3 or the kanamycin resistance cassette from the plasmid pKD4 (Datsenko, K. A. & Wanner, B. L. (2000)). The PCR product obtained was then introduced by electroporation into the recipient strain bearing the plasmid pKD46 in which the system λ☐ Red (γ, β, ☐☐exo) expressed greatly favours homologous recombination. The antibiotic-resistant transformants were then selected and the insertion of the resistance cassette was checked by PCR analysis with the appropriate oligonucleotides given in Table 2.

Protocol 2: Transduction with Phage PI for Deletion of a Gene

The DNA transfert from one *E. coli* strain to the another was performed by the technique of transduction with phage P1. The protocol was in two steps, (i) the preparation of the phage lysate on the donor strain with a single gene modified and (ii) the transduction of the recipient strain by this phage lysate.

Preparation of the Phage Lysate

Seeding with 100 µl of an overnight culture of the strain MG1655 with a single gene modified of 10 ml of LB+Cm 30 µg/ml/Km 50 µg/ml+glucose 0.2%+CaCl$_2$ 5 mM.

Incubation for 30 min at 37° C. with shaking.

Addition of 100 µl of phage lysate P1 prepared on the donor strain MG1655 (approx. 1×10$^9$ phage/ml).

Shaking at 37° C. for 3 hours until all cells were lysed.

Addition of 200 µl of chloroform, and vortexing.

Centrifugation for 10 min at 4500 g to eliminate cell debris.

Transfer of supernatant in a sterile tube and addition of 200 µl of chloroform.

Storage of the lysate at 4° C.

Transduction

Centrifugation for 10 min at 1500 g of 5 ml of an overnight culture of the *E. coli* recipient strain in LB medium.

Suspension of the cell pellet in 2.5 ml of MgSO$_4$ 10 mM, CaCl$_2$ 5 mM.

Control tubes: 100 µl cells
 100 µl phages P1 of the strain MG1655 with a single gene modified.
Tube test: 100 µl of cells+100 µl phages P1 of strain MG1655 with a single gene modified.
Incubation for 30 min at 30° C. without shaking.
Addition of 100 µl sodium citrate 1 M in each tube, and vortexing.
Addition of 1 ml of LB.
Incubation for 1 hour at 37° C. with shaking
Plating on dishes LB+Cm 30 µg/ml/Km 50 µg/ml after centrifugation of tubes for 3 min at 7000 rpm.
Incubation at 37° C. overnight.

The antibiotic-resistant transformants were then selected and the insertion of the deletion was checked by a PCR analysis with the appropriate oligonucleotides given in Table 2.

Protocol 3: Introduction of a PCR Product for Recombination and Selection of the Recombinants (Cre-LOX System)

The oligonucleotides chosen and given in Table 1 for replacement of a gene or an intergenic region were used to amplify either the chloramphenicol resistance cassette from the plasmid loxP-cm-loxP (Gene Bridges) or the neomycin resistance cassette from the plasmid loxP-PGK-gb2-neo-loxP (Gene Bridges). The PCR product obtained was then introduced by electroporation into the recipient strain bearing the plasmid pKD46 in which the system λ☐ Red (γ, β, ☐☐exo) expressed greatly favours homologous recombination. The antibiotic-resistant transformants were then selected and the insertion of the resistance cassette was checked by PCR analysis with the appropriate oligonucleotides given in Table 2.

TABLE 1

Oligonucleotides used for the constructions described in the following examples

| Gene | Names of oligos | SEQ ID N° | Sequences |
|---|---|---|---|
| uxaCAOme | 1506-DuxaCA-SMC F | N° 1 | GCAAGCTAGCTCACTCGTTGAGAGGAAGACGAAAATGA CTCCGTTTATGACTGAAGATTTCCTGTTAGATACCGTCAC ACTGGCTCACCTTCGGGTGGGCCTTTCTGCTGTAGGCTG GAGCTGCTTCG |
| Ome | 1507-DuxaCA-SMC R | N° 2 | TTAACAACTCATTTCGACTTTATAGCGTTACGCCGCTTTT GAAGATCGCCGAATTCGAGCTCGGTACCCGGGGATCCAT CTCGAGATCCGCGGATGTATACATGGGCCCCATATGAAT ATCCTCCTTAG |
| uxaCAOme | 1515-uxaCA R2 | N° 3 | CCCACTGGCCTGTAATATGTTCGG |
| Ome | 1516-uxaCA F2 | N° 4 | ATGCGATATCGACCGTATAAGCAGCAGAATAGGC |
| cI857TTadcca-cI857-icd F | | N° 5 | GCCTACAGGGCCCGTATACTAAAAATAAGAGTTACCTTA AATGGTAACTCTTATTTTTTTTATCAGCCAAACGTCTCTT CAGGCCACTGACTAGCGATAACTTTCCCCAC |
| | PR/RBS01*2-icd-TT02 R | N° 6 | GCCTTGTGCCGGAACAACTACTTTACTTTCCATTTATAAC CTCCTTAGTACATGCAACCATTATCACCGCCAGAGGTAA AATAGTCAACACGC |
| Icd | PR/RBS01*2-icd-TT02 F | N° 7 | GCGTGTTGACTATTTTACCTCTGGCGGTGATAATGGTTG CATGTACTAAGGAGGTTATAAATGGAAAGTAAAGTAGT TGTTCCGGCACAAGGC |
| | TT02-icd R | N° 8 | CTAGATATCAACAGATAAAACGAAAGGCCCAGTCTTTCG ACTGAGCCTTTCGTTTTATTTGATGTTACATGTTTTCGAT GATCGCGTCACC |
| Icd | ymfC-TT07 F | N° 9 | CTAAAAGAAGTTTTTGCATGGTATTTTCAGAGATTATG AATTGCCGCATTTCACACTGGCTCACCTTCGGGTGGGCC TTTCTGCTGTAGGCTGGAGCTGCTTCG |
| | PT01-R | N° 10 | CACCGCCAGAGGTAAAATAGTCAACACGCACGGTGTTA GATATTTATCCC |
| | PR01-F | N° 11 | GGGATAAATATCTAACACCGTGCGTGTTGACAATTTTAC CTCTGGCGGTG |
| | icd-R | N° 12 | GGGATAATCGGATTTTCAGGAACGTTGAGTTTGCCG |

TABLE 1-continued

Oligonucleotides used for the constructions described in the following examples

| Gene | Names of oligos | SEQ ID N° | Sequences |
|---|---|---|---|
| aceK | Oag 0074-DaceK-loxP R | N° 13 | GCCGCGTGGCCTGGAATTATTGATTGCTCAAACCATTTT GCAAGGCTTCGATGCTCAGTATGGTCGATTCCTCGAAGT GACCAATTAACCCTCACTAAAGGG |
|  | Oag 0075-DaceK-loxP F | N° 14 | AACATCTTCCACATGCCCTTCACGTATGCGGTTTTGTAGT GCGCGCCAGTAATCAGCGCGGAACAGGTCGGCGTGCAT CTAATACGACTCACTATAGGG |

TABLE 2

Oligonucleotides used for checking the insertion of a resistance cassette or the loss of a resistance cassette

| Gene | Names of oligos | SEQ ID N° | Homology with chromosomal region | sequences |
|---|---|---|---|---|
| uxaCA | Ome 1612-uxaCA R3 | N° 15 | 3238294-3238314 | GGTGTGGTGGAAAATTCGTCG |
|  | Ome 1774-DuxaCA F | N° 16 | 3243344-3243325 | GCATTACGATTGCCCATACC |
| icd | Ome 704 seq Ptrc-icd F | N° 17 | 1194153-1194173 | CAGAGATTATGAATTGCCGCA |
|  | Ome 705 seq Ptrc-icd R | N° 18 | 1194540-1194520 | CCAGGAGATTTTACGCTCGCC |
| aceK | Ome 0169-BAK F | N° 19 | 4218284-4218258 | AACGCATTACCCACTCTGTTTAA TACG |
|  | Ome 0701-aceK F | N° 20 | 4216085-4216103 | CTTATCATGCCTACAGCCG |

EXAMPLE 1

Construction of a Thermo Inducible Strain to Produce Glycolic Acid by Fermentation: MG1655 Ptrc50/RBSB/TTG-icd::Cm ΔuxaCA::RN/TTadcca-cI857-PR/RBS01*2-icd-TT02::Km ΔaceB Δgcl ΔglcDEFGB ΔaldA ΔiclR Δedd+eda ΔpoxB ΔackA+pta (pME101-ycdW-TT07-PaceA-aceA-TT01)

The strain E. coli MG1655 Ptrc50/RBSB/TTG-icd::Cm ΔaceB Δgcl ΔglcDEFGB ΔaldA ΔiclR Δedd+eda ΔpoxB ΔackA+pta (pME101-ycdW-TT07-PaceA-aceA-TT01) was built according to the description given in patent application WO 2010/108909.

1. Construction of the Strain MG1655 ΔuxaCA::RN/TTadcca-cI857-PR/RBS01*2-icd-TT02::Km To replace the uxaCA region by the TTadcca-cI857-PR/RBS01*2-icd-TT02 fragment, we used the homologous recombination strategy described by Datsenko & Wanner (2000) and detailed in Protocol 1. This strategy allows the insertion of a kanamycin resistance cassette and additional DNA, while deleting most of the region concerned.

The plasmid pUC18-DuxaCA-RN/TTadcca-cI857-PR/RBS01*2-icd-TT02 was built for this purpose as detailed below.

The fragment TTadcca-cI857-PR/RBS01*2-icd-TT02 was synthesized by PCR and cloned into the vector pUC18-DuxaCA-SMC-Km (SMC for Multiple Cloning Site).

To build the plasmid pUC18-DuxaCA-SMC-Km, the DuxaCA-SMC-Km fragment was obtained by PCR on the MG1655 DuxaCA-SMC-Km genomic DNA as template and cloned into pUC18 (Norrander et al., 1983, Gene 26, 101-106).

Construction of the Strain MG1655 DuxaCA-SMC-Km:

To replace the uxaCA region by the SMC-Km one, we used the homologous recombination technique and a PCR product synthesized with oligonucleotides Ome 1506-D uxaCA-SMC F and Ome 1507-D uxaCA-SMC R given in table 1 (Seq. No. 1 and No. 2).

Ome 1506-D uxaCA-SMC F (SEQ ID NO 1)
*GCAAGCTAGCTCACTCGTTGAGAGGAAGACGAAAATGACTCCGTTTATG*

*ACTGAAGATTTCCTGTTAGATACCG*<u>TCACACTGGCTCACCTTCGGGTGG</u>

<u>GCCTTTCTGCTGTAGGCTGGAGCTGCTTCG</u> with
- a region (italic upper case) homologous to the sequence (3242797-3242724) of the region uxaCA (reference sequence on the website http://ecogene.org/),
- a region (underlined upper case) for T7Te transcriptional terminator sequence from T7 phage (Harrington K. J., Laughlin R. B. and Liang S. Proc Natl Acad Sci U S A. 2001 Apr. 24; 98 (9):5019-24.),
- a region (upper case) for the amplification of the kanamycin resistance cassette (reference sequence in Datsenko, K. A. & Wanner, B. L., 2000, *PNAS*, 97: 6640-6645), Ome 1507-D uxaCA-SMC R (SEQ ID NO 2)
*TTAACAACTCATTTCGACTTTATAGCGTTACGCCGCTTTTGAAGATCGCC*

<u>GAATTCGAGCTCGGTACCCGGGGATCCATCTCGAGATCCGCGGATGTATA</u>

<u>CATGGGCCC</u>CATATGAATATCCTCCTTAG with
- a region (italic upper case) homologous to the sequence (3239830-3239879) of the region uxaCA (reference sequence on the website http://ecogene.org/),
- a region (underlined upper case) for the SMC habouring with ApaI, BstZ17I, SacII, XhoI, AvaI, BamHI, SmaI, KpnI, SacI, EcoRI restriction sites
- a region (upper case) for the amplification of the kanamycin resistance cassette (reference sequence in Datsenko, K. A. & Wanner, B. L., 2000, PNAS, 97: 6640-6645), The resulting PCR product was introduced by electroporation into the strain MG1655 (pKD46). Then, the kanamycin-resistant transformants were selected, and the insertion of the antibiotic cassette was checked by PCR analysis with the oligonucleotides Ome 1612-uxaCA_R3 and Ome 1774-DuxaCA_F showed in Table 2 (Seq. No. 15 and No. 16). The selected clones were validated by DNA sequencing. The final strain was named MG1655 DuxaCA-SMC-Km.

Construction of the plasmid pUC18-DuxaCA-SMC-Km:

The DuxaCA-SMC-Km region was amplified by PCR from genomic DNA of the strain MG1655 DuxaCA-SMC-Km as template and oligonucleotides Ome 1515-uxaCA R2 and Ome 1516-uxaCA F2 showed in Table 1 (Seq. No. 3 and No. 4):

```
Ome 1515-uxaCA R2
                                     (SEQ ID NO 3)
CCCACTGGCCTGTAATATGTTCGG
``` homologous to the downstream region of uxaCA (from 3239021 to 3239044)

```
Ome 1516-uxaCA F2
                                     (SEQ ID NO 4)
ATGCGATATCGACCGTATAAGCAGCAGAATAGGC
``` with
- a region (upper case) with extra-bases
- a region (underlined, upper case) harbouring the EcoRV restriction site
- a region (italic upper case) homologous to the upstream region of uxaCA (from 3243425 to 3243402)

Then, the PCR product (obtained with a blunt-end DNA polymerase) was cleaved by the restriction enzyme EcoRV and cloned into the SmaI site of pUC18. The resulting plasmid was checked by sequencing and named pUC18-DuxaCA-SMC-Km.

For the construction of the plasmid pUC18-TTadcca-cI857-PR/RBS01*2-icd-TT02, the fragment TTadcca-cI857-PR/RBS01*2-icd-TT02 was synthesized by PCR and cloned into the plasmid pUC18-DuxaCA-SMC-Km described above.

In a first step, the TTadcca-cI857-PR/RBS01*2 region was amplified by PCR from the pFC1 vector as template (Mermet-Bouvier & Cliauvat, 1994, Current Microbiology, vol. 28, pp 145-148) and oligonucleotides TTadcca-cI857-icdF and PR/RBS01*2-icd-TT02 R listed in Table 1 (Seq. No. 5 and No. 6). In a second step, the fragment icd-TT02 was amplified by PCR from the MG1655 genomic DNA using the oligonucleotides PR/RBS01*2-icd-TT02 F and TT02-icd R (Seq. N° 7 and N° 8). In a third step, the TTadcca-cI857-PR/RBS01*2-icd-TT02 region was synthesized by PCR using a mix of TTadcca-cI857-PR/RBS01*2 and icd-TT02 PCR products as template and the oligonucleotides TTadcca-cI857-icd F and TT02-icd R (Seq. No. 5 and No. 8). This final PCR product was cloned into the pSCB vector (Stratagene) and the resulting plasmid was verified by sequencing and named pSCB-TTadcca-cI857-PR/RBS01*2-icd-TT02.

with

```
TTadcca-cI857-icd F
                                     (SEQ ID NO 5)
GCCTACAGGGCCCGTATACTAAAAATAAGAGTTACCTTAAATGGTAACT

CTTATTTTTTTTATCAGCCAAACGTCTCTTCAGGCCACTGACTAGCGAT

AACTTTCCCCAC
```

- a region (upper case) with extra-bases,
- a region (underlined, upper case) harbouring the ApaI and BstZ17I restriction sites,
- a region (italic upper case) for TTadcca transcriptional terminator sequence (transcription terminator of the adc gene from Clostridium acetobutylicum, homologous from 179847 to 179807 of the pSOL1 megaplasmid),
- a region (upper bold case) homologous to the 3' extremity of the cI857 gene

```
PR/RBS01*2-icd-TT02 R
                                     (SEQ ID NO 6)
GCCTTGTGCCGGAACAACTACTTTACTTTCCATTTATAACCTCCTTAGT

ACATGCAACCATTATCACCGCCAGAGGTAAAATAGTCAACACGC
``` with
- a region (upper case) homologous to the 5' extremity of the icd gene (from 1194378 to 1194346)
- a region (underlined upper case) homologous to the lambda bacteriophage $P_R$ promoter, except 5 bases (underlined upper italic case) to obtain the RBS01*2 version of the RBS to create a PsiI restriction site.

```
PR/RBS01*2-icd-TT02 F
                                     (SEQ ID NO 7)
GCGTGTTGACTATTTTACCTCTGGCGGTGATAATGGTTGCATGTACTAA

GGAGGTTATAAATGGAAAGTAAAGTAGTTGTTCCGGCACAAGGC
``` with
- a region (upper case) homologous to the 5' extremity of the icd gene (from 1194346 to 1194378)
- a region (underlined upper case) homologous to the lambda bacteriophage Pr promoter, except 5 bases (underlined upper italic case) to obtain the RBS01*2 version of the RBS to create a PsiI restriction site.

```
TT02-icd R
                                     (SEQ ID NO 8)
CTAGATATCAACAGATAAAACGAAAGGCCCAGTCTTTCGACTGAGCCTT

TCGTTTTATTTGATGTTACATGTTTTCGATGATCGCGTCACC
``` with
- a region (upper case) with extra-bases,
- a region (italic upper case) harbouring the EcoRV restriction site,
- a region (underlined upper case) homologous to the TT02 transcriptional terminator sequence corresponding to the transcription terminator $T_1$ of the rrnB gene of E. coli (Orosz A, Boros I and Venetianer P. Eur. J. Biochem. 1991 Nov. 1; 201 (3):653-9),
- a region (upper bold case) homologous to the 3' extremity of the icd gene (from 1195596 to 1195570)

To transfer the TTadcca-cI857-PR/RBS01*2-icd-TT02 fragment on the vector pUC18-DuxaCA-SMC-Km, the plasmid pSCB-TTadcc-cI857-PR/RBS01*2-/W-TT02 was restricted by restriction enzymes ApaI and EcoRV and the resulting TTadcca-cI857-PR/RBS01*2-icd-TT02 fragment cloned into ApaI/SmaI sites of the vector pUC18-DuxaCA-SMC-Km, leading to the vector pUC18-DuxaCA-RN/TTadcca-cI857-PR/RBS01*2-icdTT02::Km.

Finally, in order to replace by homologous recombination the uxaCA region by TTadcca-cI857-PR/RBS01*2-icd-TT02::Km, the plasmid pUC18-DuxaCA-RN/TTadcca-cI857-PR/RBS01*2-icd-TT02::Km was restricted by MluI and NruI and the DNA fragment DuxaCA-RN/TTadcca-cI857-PR/RBS01*2-icd-TT02::Km was introduced by electroporation into the strain MG1655 (pKD46). Then, the kanamycin-resistant transformants were selected, and the insertion of DuxaCA-RN/TTadcca-cI857-PR/RBS01*2-icd-TT02::Km into the chromosome was checked by a PCR analysis with the oligonucleotides Ome 1612-uxaCA_R3 and Ome 1774-DuxaCA_F (Seq. N° 15 and N° 16). The strain was named MG1655 DuxaCA-RN/TTadcca-cI857-PR/RBS01*2-icd-TT02::Km.

2. Construction of the Strain MG1655 Ptrc50/RBSB/TTG-icd::Cm  ΔuxaCA::RN/TTadcca-cI857-PR/RBS01*2-icd-TT02::Km ΔaceB Δgcl ΔglcDEFGB ΔaldA ΔiclR Δedd+eda ΔpoxB ΔackA+pta (pME101-ycdW-TT07-PaceA-aceA-TT01)

To replace the uxaCA region by TTadcca-cI857-PR/RBS01*2-icd-TT02::Km in the MG1655 Ptrc50/RBSB/TTG-icd::Cm ΔaceB Δgcl ΔglcDEFGB ΔaldA ΔiclR Δedd+eda ΔpoxB ΔackA+pta (pME101-ycdW-TT07-PaceA-aceA-TT01) strain, the construction ΔuxaCA::RN/TTadcca-cI857-PR/RBS01*2-icd-TT02::Km was transferred by P1 phage transduction (see Protocol 2) from the strain MG1655 ΔuxaCA::RN/TTadcca-cI857-PR/RBS01*2-icd-TT02::Km into the strain MG1655 Ptrc50/RBSB/TTG-icd::Cm ΔaceB Δgcl ΔglcDEFGB ΔaldA ΔiclR. Δedd+eda ΔpoxB ΔackA+pta. The antibiotics resistant transformants were selected and the insertion of ΔuxaCA::RN/TTadcca-cI857-PBS01*2-icd-TT02::Km on the chromosome was checked by PCR analysis with oligonucleotides Ome 1612-uxaCA_R3 (seq. N° 15) and Ome 1774-DuxaCA_F (seq N° 16). The resulting strain was named MG1655 Ptrc50/RBSB/TTG-icd::Cm ΔuxaCA::RN/TTadcca-cI857-PR/RBS01*2-icd-TT02::Km ΔaceB Δgcl ΔglcDEFGB ΔaldA ΔiclR Δedd+eda ΔpoxB ΔackA+pta.

The plasmid pME101-ycdW-TT07-PaceA-aceA-TT01 (previously described in patent applications EP 09155971,6 and U.S. 61/162,712) was finally introduced by electroporation to lead to the MG1655 Ptrc50/RBSB/TTG-icd::Cm ΔuxaCA::RN/TTadcca-cI857-PR/RBS01*2-icd-TT02::Km ΔaceB Δgcl ΔglcDEFGB ΔaldA ΔiclR Δedd+eda ΔpoxB ΔackA+pta (pME101-ycdW-TT07-PaceA-aceA-TT01) named AG1385.

EXAMPLE 2

Construction of a Thermo Inducible Strain to Produce Glycolic Acid by Fermentation: MG1655 TTadcca/CI857/PR01/RBS01*2-icd::Km ΔaceB Δgcl ΔglcDEFGB ΔaldA ΔiclR Δedd+eda ΔpoxB ΔackA+pta ΔaceK::Cm (pME101-ycdW-TT07-PaceA-aceA-TT01)

The strain E. coli MG1655 ΔaceB Δgcl ΔglcDEFGB ΔaldA ΔiclR Δedd+eda ΔpoxB ΔackA+pta (pME101-ycdW-TT07-PaceA-aceA-TT01) was built according to the description given in patent applications EP 09155971,6 and U.S. 61/162,712.

1. Construction of the Strain MG1655 TTadcca-cI857-PR01/RBS01*2-icd::Km

The natural icd promoter was replaced in the strain E. coli MG1655 by the DMA fragment TTadcca-cI857-PR01/RBS01*2::Km. To replaced the natural icd promoter by the TTadcca-cI857-PR01/RBS01*2 DNA fragment, we used the homologous recombination strategy described by Datsenko & Wanner (2000). The construction was performed according to the technique described in Protocol 1.

To construct the MG1655 TTadcca-cI857-PR01/RBS01*2-icd::Km strain, the gene cI857, the promoter PR01 and the kanamycin cassette (Km) were amplified by PCR on the MG1655 ΔuxaCA::RN/TTadcca-cI857-PR/RBS01*2-icd-TT02::Km genomic DNA with oligonucleotides described in Table 1 (Seq. No. 9, No. 10, No. 11 and No. 12).

ymfC-TT07 F (SEQ ID NO 9)
CTAAAAGAAGTTTTTTGCATGGTATTTTCAGAGATTATGAATTGCCGCA

TTTCACACTGGCTCACCTTCGGGTGGGCCTTTCTGCTGTAGGCTGGAGC

TGCTTCG with
- a region (upper case) homologous to the 5' extremity of the ymfC gene (from 1194125 to 1194175)
- a region (underlined upper case) for T7Te transcriptional terminator sequence from T7 phage (Harrington K. J., Laughlin R. B. and Liang S, 2001, PNAS Apr 24; 98 (9):5019-24.),
- a region (upper bold case) for the amplification of the kanamycin resistance cassette (reference sequence in Datsenko, K. A. & Wanner, B. L., 2000, PNAS, 97: 6640-6645),

PR01-R (SEQ ID NO 10)
CACCGCCAGAGGTAAAATAGTCAACACGCACGGTGTTAGATATTTATCCC homologous to the lambda bacteriophage $P_R$ promoter, except 1 base (bold upper case) to obtain the PR01 mutant version of the $P_R$ promoter

PR01-F (SEQ ID NO 11)
GGGATAAATATCTAACACCGTGCGTGTTGACAATTTTACCTCTGGCGGTG homologous to the lambda bacteriophage $P_R$ promoter, except 1 base (bold, upper case) to obtain the PR01 mutant version of the $P_R$ promoter icd-R (SEQ ID NO 12)
GGGATAATCGGATTTTCAGGAACGTTGAGTTTGCCG homologous to the icd gene (from 1194434 to 1194399)

The PCR fragment TTadcca-cI857-PR01/RBS01*2-icd::Km was first introduced by electroporation into the strain MG1655 (pKD46) to give the strain MG1655 TTadcca-cI857-PR01/RBS01*2-icd::Km. Kanamycin resistant transformants were selected. The insertion of the TTadcca-cI857-PR01/RBS01*2-icd::Km fragment was checked by PCR analysis with oligonucleotides Ome 704 seq Ptrc-icd F and Ome 705 seq Ftrc-icd R listed in Table 2 (Seq. No. 17 and No. 18) and then validated by sequencing. The resulting strain was named MG1655 TTadcca-cI857-PR01/RBS01*2-icd::Km.

2. Construction of the Strain MG1655 TTadcca/CI857/PR01/RBS01*2-icd::Km ΔaceB Δgcl ΔglcDEFGB ΔaldA ΔiclR Δedd+eda ΔpoxB ΔackA+pta ΔaceK::Cm (pME101-ycdW-TT07-PaceA-aceA-TT01)

The construction TTadcca-cI857-PR01/RBS01*2-icd::Km was transferred by transduction (see Protocol 2) from the donor strain MG1655 TTadcca-cI857-PR01/RBS01*2-icd::Km to the receiver strain MG1655 ΔaceB Δgcl ΔglcDEFGB ΔaldA ΔiclR Δedd+eda ΔpoxB ΔackA+pta strain. Then, kanamycin-resistant transformants were selected and the insertion of the TTadcca-cI857-PR01/RBS01*2-icd-TT02::Km region was checked by PCR analysis with the oligonucleotides Ome 704 seq Ptrc-icd F (seq No. 17) and Ome 705 seq Ptrc-icd R (seq No. 18). The strain was named. MG1655 TTadcca-cI857-PR01/RBS01*2-icd-TT02::Km ΔaceB Δgcl ΔglcDEFGB ΔaldA ΔiclR Δedd+eda ΔpoxB ΔackA+pta.

The gene aceK was deleted in the strain *E. coli* MG1655 TTadcca-cI857-PR01/RBS01*2-icd-TT02::Km ΔaceB Δgcl ΔglcDEFGB ΔaldA ΔiclR Δedd+eda ΔpoxB ΔackA+pta (pKD46) by homologous recombination as previously described using the oligonucleotides Ome 0205-DaceBAKR and Ome 0700-DaceK F (Seq. No. 13 and No. 14) described in table 1 (See Protocol 3).

```
Oag 0074-DaceK-loxP R
                                          (SEQ ID NO 13)
GCCGCGTGGCCTGGAATTATTGATTGCTCAAACCATTTTGCAAGGCTTC

GATGCTCAGTATGGTCGATTCCTCGAAGTGACCAATTAACCCTCACTAA

AGGG
``` with
- a region (upper case) homologous to the sequence (4216621-4216702) of the gene aceK (reference sequence on the website http://ecogene.org/),
- a region (underlined upper case) for the amplification of the chloramphenicol resistance cassette (reference sequence Gene Bridges),

```
Oag 0075-DaceK-loxP F
                                          (SEQ ID NO 14)
AACATCTTCCACATGCCCTTCACGTATGCGGTTTTGTAGTGCGCGCCAGT

AATCAGCGCGGAACAGGTCGGCGTGCATCTAATACGACTCACTATAGGG
``` with
- a region (upper case) homologous to the sequence (4218298-4218220) of the gene aceK (reference sequence on the website http://ecogene.org/).
- a region (underlined upper case) for the amplification of the chloramphenicol resistance cassette (reference sequence Gene Bridges).

Chloramphenicol and kanamycin resistant transformants were then selected and verified by PCR analysis with the oligonucleotides Ome 0.169-BAK F and Ome 0701-aceK F listed in Table 2 (Seq. No. 19 and No. 20). In the last step, the plasmid pME101-ycdW-TT07-PaceA-aceA-TT01 was introduced into the strain MG1655 TTadcca-cI857-PR01/RBS01*2-icd-TT02::Km ΔaceB Δgcl ΔglcDEFGB ΔaldA ΔiclR Δedd+eda ΔpoxB ΔackA+pta ΔaceK::Cm. The final strain MG1655 TTadcca-cI857-PR01/RBS01*2-icd-TT02::Km ΔaceB Δgcl ΔglcDEFGB ΔaldA ΔiclR Δedd+eda ΔpoxB ΔackA+pta ΔaceK::Cm (pME101-ycdW-TT07-PaceA-aceA-TT01) was named AG1413.

Fermentation of Producer Strains

Glycolic acid production was determined in the thermo inducible strains AG1385 and AG1413. Construction of these strains has been described in examples 1 and 2. Genotypes of the strains used below:

AG0662: MG1655 Ptrc50/RBSB/TTG-icd::Cm ΔaceB Δgcl ΔglcDEFGB ΔaldA ΔiclR Δedd+eda ΔpoxB ΔackA+pta (pME101-ycdW-TT07-PaceA-aceA-TT01)

Construction of AG0662 was described in patent applications WO 2007/141316A, U.S. 61/162,712 and EP 09155971.6.

AG1385: MG1655 Ptrc50/RBSB/TTG-icd::Cm ΔuxaCA::RN/TTadcca-cI857-PR/RBS01*2-icd-TT02::Km ΔaceB Δgcl ΔglcDEFGB ΔaldA ΔiclR Δedd+eda ΔpoxB ΔackA+pta (pME101-ycdW-TT07-PaceA-aceA-TT01)

AG1413: MG1655 TTadcca/CI857/PR01/RBS01*2-icd::Km ΔaceB Δgcl ΔglcDEFGB ΔaldA ΔiclR Δedd+eda ΔpoxB ΔackA+pta ΔaceK::Cm (pME101-ycdW-TT07-PaceA-aceA-TT01)

Strain AG0662 possesses an attenuated expression of Icd gene. Whatever the temperature of the culture is, the isocitrate dehydrogenase activity (ICD) of the cells is around 50 mUI/mg (table 4).

Strains AG1385 and AG1413 have a thermo inducible copy of icd gene. At 37° C., Icd expression is maximal and ICD activity is above 1000 mUI/mg, whereas at 30° C., icd expression is repressed and ICD activity is around 50 to 100 mUI/mg (see example 5).

EXAMPLE 3

Fermentation Cultures of Strains AG0662, AG1385 and AG1413 to Produce Glycolic Acid in Industrial-like Conditions To assay the stability of strains AG0662, AG1385 and AG1413, they were cultivated successively for 30 generations, corresponding to a minimum number for an industrial process, before determining their performance in fermentors.

For this purpose between 3 and 5 cultures of each strain were carried out successively in baffled flasks in synthetic medium MML8AG1_100 (See composition in table 1), which was supplemented with 40 g/l of MOPS and 10 g/l of glucose. Flasks were agitated at 37° C. during 2 days (final OD between 6 and 8) at 200 rpm.

TABLE 1

| Composition of minimal medium MML8AG1 100. | |
|---|---|
| Constituent | Concentration (g/l) |
| Citric acid | 6.00 |
| $MgSO_4\ 7H_2O$ | 1.00 |
| $CaCl_2\ 2H_2O$ | 0.04 |
| $CoCl_2\ 6H_2O$ | 0.0080 |
| $MnSO_4\ H_2O$ | 0.0200 |
| $CuCl_2\ 2H_2O$ | 0.0020 |
| $H_3BO_3$ | 0.0010 |
| $Na_2MoO_4\ 2H_2O$ | 0.0004 |
| $ZnSO_4\ 7H_2O$ | 0.0040 |
| $Na_2HPO_4$ | 2.00 |
| $K_2HPO_4\ 3H_2O$ | 10.48 |
| $(NH_4)_2HPO_4$ | 8.00 |
| $(NH_4)_2SO_4$ | 5.00 |
| $NH_4Cl$ | 0.13 |
| $FeSO_4\ 7H_2O$ | 0.04 |
| Thiamine | 0.01 |

Successive cultures were also grown in 700 mL working volume vessels assembled on a Multifors Multiple Fermentor System (Infors), Each vessel was filled up with 200 ml of synthetic medium MML11AG1_100 supplemented with 20 g/l of glucose and 50 mg/l of spectinomycin and inoculated to an OD between 0.01 and 0.8.

TABLE 2

Composition of minimal medium MML11AG1 100.

| Constituent | Concentration (g/l) |
| --- | --- |
| Citric acid | 3.00 |
| $MgSO_4\ 7H_2O$ | 1.00 |
| $CaCl_2\ 2H_2O$ | 0.04 |
| $CoCl_2\ 6H_2O$ | 0.0080 |
| $MnSO_4\ H_2O$ | 0.0200 |
| $CuCl_2\ 2H_2O$ | 0.0020 |
| $H_3BO_3$ | 0.0010 |
| $Na_2MoO_4\ 2H_2O$ | 0.0004 |
| $ZnSO_4\ 7H_2O$ | 0.0040 |
| $KH_2PO_4$ | 0.70 |
| $K_2HPO_4\ 3H_2O$ | 1.17 |
| $NH_4H_2PO_4$ | 2.99 |
| $(NH_4)_2HPO_4$ | 3.45 |
| $(NH_4)_2SO_4$ | 8.75 |
| $NH_4Cl$ | 0.13 |
| $FeSO_4\ 7H_2O$ | 0.04 |
| Thiamine | 0.01 |

Cultures were carried out at 37° C. with an aeration of 0.2 lpm and dissolved oxygen was maintained above 30% saturation by controlling agitation (initial: 300 rpm; max: 1200 rpm) and oxygen supply (0 to 40 ml/min). The pH was adjusted at pH 6.8±0.1 by the addition of base (mix of NH4OH 7.5% w/w and NaOH 2.5% w/w). The fermentation was carried out in discontinuous fed-batch mode, with a feed solution of 700 g/l of glucose (See table 3). When glucose was used up in the culture medium, a pulse of fed restored a concentration of 20 g/l of glucose.

TABLE 3

Composition of feed solution.

| Constituent | Concentration (g/l) |
| --- | --- |
| Glucose | 700.00 |
| $MgSO_4\ 7H_2O$ | 2.00 |
| $CoCl_2\ 6H_2O$ | 0.0256 |
| $MnSO_4\ H_2O$ | 0.0640 |
| $CuCl_2\ 2H_2O$ | 0.0064 |
| $H_3BO_3$ | 0.0032 |
| $Na_2MoO_4\ 2H_2O$ | 0.0013 |
| $ZnSO_4\ 7H_2O$ | 0.0128 |
| $FeSO_4\ 7H_2O$ | 0.08 |
| Thiamine | 0.01 |

After 30 generations grown at 37° C., populations were sampled and stored in glycerol at −80° C. (dilution in sterile glycerol solution at 40% w/w).

Each population was then tested for production of glycolic acid.

Fermentation conditions used for strain AG0662 and its derived population (30 generations) have already been described in patent applications EP 09155971.6 and EP09171297.6.

The fermentation process used for the thermo inducible strains AG1385 and AG1413 is described in example 4 below.

Glycolic acid production of strains AG0662, AG1385 and AG1413 and their respective derived populations (±30 generations) are presented in table 4.

TABLE 4

Performances of strains AG0662 (with an attenuated expression of icd), AG1385 and AG1413 (thermo induction on icd) and their respective populations determined at 30° C. (production phase). Performances and isocitrate dehydrogenase (ICD) activities of the cells correspond to one time point at the same OD for all conditions.

| strain | Titre [GA] (g/l) | Yield (g GA/g glucose) | Productivity (g/l/h) | ICD activity (mUI/mg) |
| --- | --- | --- | --- | --- |
| AG0662 | 15.5 | 0.32 | 0.70 | 54 |
| Population of AG0862 + 30 generations | 1.3 | 0.05 | 0.21 | 1045 |
| AG1385 | 42.6 | 0.31 | 1.29 | 62 |
| Population of AG1385 + 30 generations | 41.3 | 0.30 | 1.25 | 103 |
| AG1413 | 43.1 | 0.32 | 1.28 | 57 |
| Population of AG1413 + 30 generations | 41.7 | 0.34 | 1.24 | 48 |

As can be seen in table 4, strain AG0662 is highly unstable, since the performances of the strain when cultured for 30 generations before the performance test are much lower than without additional cultivation before the test.

Loss of performances is also linked to a higher ICD activity (table 4).

All mutation that can improve icd expression and so ICD activity of the cell will improve growth rate and decrease the yield of production. Population of AG0662 has evolved and recombined to lead, to a higher expression of icd. ICD activity in this population is 10 times higher than in the mother strain (1045 mUI/mg instead of 50 mUI/mg).

In contrast, performances of both strains harbouring a thermo inducible promoter that drives icd expression (AG1385 and AG1413) do only slightly vary in the performance test when the two conditions (I) without or (II) with growth for 30 generations before the test are compared. Thus the presence of a thermo inducible icd gene in the glycolic acid producer strains improves the strain stability.

Isocitrate dehydrogenase activity (ICD) was measured for each strain and each population at the same OD according to the protocol described in example 5.

For a maximal production of glycolic acid, activity of ICD must be low; around 50 to 100 mUI/mg.

EXAMPLE 4

Fermentation Process for Thermo Inducible Strains

The protocol used for thermo inducible strains is based on the "pH increase" protocol described in patent EP 09171297.6 with specific modification due to the thermo regulation of icd gene.

Fermentations were realized with strains AG1385 and AG1413.

For each strain, an independent preculture was carried out in a 500 ml baffled Erlenmeyer flask filled with 55 ml synthetic medium MML8AG1_100 supplemented with 40 g/l of MOPS and 10 g/l of glucose, at 37° C. during 2 days (OD between 7 and 10). 20 mL of each preculture were used to inoculate fermenters.

Cultures were grown in 700 ml, working volume vessels assembled on a Multifors Multiple Fermentor System (Infors). Each vessel was filled with 200 ml of synthetic medium MML11AG1_100 supplemented, with 20 g/l of glucose and 50 mg/l of spectinomycin and inoculated at an OD of about 1.

Cultures were carried out at 30° C. with an aeration of 0,2 lpm and dissolved oxygen was maintained above 30% saturation by controlling agitation (initial: 300 rpm; max: 1200 rpm) and oxygen supply (0 to 40 ml/min).

pH was adjusted at pH 6.8±0.1 by the addition of base (mix of NH4OH 7.5 % w/w and NaOH 2.5% w/w). The fermentation was carried out in discontinuous fed-batch mode, with a feed solution of 700 g/l glucose.

When the glucose was used up in the culture medium, a pulse of fed restored a concentration of 20 g/l of glucose.

After the 5$^{th}$ pulse of fed (100 g/L of glucose consumed), pH was adjusted from 6.8 to 7.4 over an interval of 2 h and kept constant until the end of the culture.

Glycolic acid production of strains AG1385 and AG1413 grown under these conditions are given in table 5 below.

TABLE 5

Glycolic acid production of thermo inducible strains AG1385 and AG1413 at 30° C. (glycolic acid production phase) after precultures at 37° C. (biomass production phase). Mean values of 3 cultures of each strain are presented.

| Strain | [GA] titre (g/l) | Yield (g GA/g glucose) | Productivity (g/l/h) |
|---|---|---|---|
| AG1385 | 51.3 ± 1.0 | 0.38 ± 0.02 | 0.99 ± 0.07 |
| AG1413 | 52.5 ± 1.0 | 0.36 ± 0.01 | 1.08 ± 0.07 |

EXAMPLE 5

Isocitrate Dehydrogenase (ICD) Activity Assay

To assay isocitrate dehydrogenase activity, cells (25 mg) were lysed by a Precellys (1×30 s at 6300 rpm, Bertin Technologies) and cell debris were removed by centrifugation at 12000 g (4° C.) during 30 minutes. Protein concentrations were determined by Bradford. ICD activity was determined, in a volume of 300 µL at pH 8,2 and 30° C. The assay mixture contained 50 mM Tris-HCl (pH 8,2), 50 mM MgCl$_2$, 5 mM NADP$^+$, 0,5 mM Oxalate and 3-6 µg of crude cell extract. The reaction mixture was incubated at 30° C. for 10 minutes. Then, 10 mM of Isocitrate was added to start the reaction. Changes in absorbance at 340 nm ($\in$=4,57 µmol$^{-1}$.mL.cm$^{-1}$) due to NADPH formation were monitored at 30° C. during 30 minutes.

TABLE 6

ICD activities measured on precultures and last time points of culture of AG1385 and AG1413 cultivated in Multifors according to conditions described in Example 4. PC were grown at 37° C. (biomass production phase) and main cultures at 30° C. (glycolic acid production phase).

| Strains | Conditions | ICD (mUI/mg) |
|---|---|---|
| AG1413 | PC at 37° C. | 2382 ± 12 |
|  | Culture at 30° C. | 41 ± 4 |

TABLE 6-continued

ICD activities measured on precultures and last time points of culture of AG1385 and AG1413 cultivated in Multifors according to conditions described in Example 4. PC were grown at 37° C. (biomass production phase) and main cultures at 30° C. (glycolic acid production phase).

| Strains | Conditions | ICD (mUI/mg) |
|---|---|---|
| AG1385F01 | PC at 37° C. | 974 ± 48 |
|  | Culture at 30° C. | 65 ± 3 |

REFERENCES

Michihiko Kataoka, *Biosci. Biotechnol. Biochem.*, 2001

Neidhardt, F. C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli* and *Salmonella:* Cellular and Molecular Biology. (American Society for Microbiology)

Tang X, Tan Y, Zhu H, Zhao K, Shen W. 'Microbial conversion of glycerol to 1,3-propanediol by an engineered strain of *Escherichia coli*.' Appl Environ Microbiol. 2009 March; 75 (6): 1628-34.

Anderson, 1946, *Proc. Natl. Acad. Sci. USA* 32:120-128;

Miller, 1992; A Short Course in Bacterial Genetics: A Laboratory Manual and Handbook for *Escherichia coli* and Related Bacteria, Cold Spring Harbor Laboratory Press, Cold Spring Harbor, N.Y.;

Schaefer et al. 1999, *Anal. Biochem.* 270: 88-96;

Ptashne M, 'A genetic switch'. Blackwell Scientific, Cambridge, Mass. 1986;

Ptashne M. 'A genetic switch: Phage lambda revisited'. Cold Spring Harbor Lab Press. Cold Spring Harbor, N.Y. 2004;

Little J. 'The bacteriophages, Part II: Life of phages, 8. Gene regulatory circuitry of phage λ.' 2$^{nd}$ edition 2004. Richard Calendared. Oxford University Press;

Bukrinsky et al., *Gene,* 70 (1998) 415-417;

Mandal & Lieb, 1976,

Winstanley et al., 19 89;

Sussman R, Jacob F. C. R. 'On a thermosensitive repression system in the *Escherichia coli* lambda bacteriophage'. Hebd. Seances Acad. Sci. 1962, 254, p1517;

Sambrook et al. 'Molecular Cloning: a Laboratory Manual'. 2$^{nd}$ ed. 1989 Cold Spring Harbor Lab., Cold Spring Harbor, N.Y.;

Datsenko, K. A. & Wanner, B. L., 2000, *PNAS,* 97: 6640-6645;

Norrander et al., 1983, *Gene* 26,101-106

Harrington K. J., Laughlin R. B. and Liang S. *Proc Natl Acad Sci USA.* 2001 Apr. 24; 98 (9): 5019-24;

Mermet-Bouvier & Chauvat, 1994, *Current Microbiology, vol.* 28, pp 145-148;

Orosz A, Boros I and Venetianer P. *Eur. J. Biochem.* 1991 Nov. 1; 201(3):653-9.

The invention claimed is:

1. A method for producing glycolic acid in a fermentative process comprising:
    culturing a modified microorganism in an appropriate culture medium comprising a source of carbon,
    modulating in said microorganism an expression of a target icd gene with an external stimulus, and
    recovering glycolic acid from the culture medium,
wherein, in said microorganism belonging to the *Enterobacteriaceae* genus, expression of the target icd gene involved in glycolic acid biosynthesis pathway is under control of a heterologous inducible promoter having activity that is modulated with said external stimulus, wherein said heterologous inducible promoter is selected from the group consisting of: a promoter regulated by a modified repressor of phage lambda, a modified lac promoter regulated by a temperature sensitive lac repressor, and a promoter having activity that is modulated with chemical external stimulus.

2. The method of claim 1, wherein the inducible promoter is induced by temperature and is selected from:
    promoters regulated by a modified repressor of phage lambda selected from:
        promoter PR or a derivative of said promoter PR, or
        promoter PL or a derivative of said promoter PL.

3. The method of claim 2, wherein said modified repressor of phage lambda is a temperature labile allele of a lambda repressor cI.

4. The method of claim 1, wherein in said modified microorganism, the gene recA is deleted.

5. The method of claim 1, wherein said external stimulus is a chemical stimulus, said stimulus being selected from:
    changes in repression of carbon catabolite;
    presence of specific carbon source, or
    presence of sugar alcohol.

6. The method of claim 1, wherein said inducible promoter is capable of being used to allow expression of said icd gene at 37° C. to 42° C. and represses expression of said icd gene at 28° C. to 32° C.

7. The method of claim 1, wherein recovery of produced glycolic acid in the culture medium comprises recovering one or more derivatives and/or precursors of glycolic acid present in the culture medium.

8. The method of claim 1, wherein said microorganism is from the *Escherichia coli* species.

9. The method of claim 1, wherein said microorganism presents the following genetic modifications:
    deletion of the genes aceB, gcl, glcDEFGB, aldA, iclR, edd, eda, poxB, ackA, and pta; and
    overexpression of the gene ycdW.

10. The method of claim 9, wherein said microorganism further presents a deletion of the gene aceK.

11. The method of claim 3, wherein said microorganism presents the following genetic modifications:
    deletion of the genes aceB, gcl, glcDEFGB, aldA, iclR, edd, eda, poxB, ackA, and pta; and
    overexpression of the gene ycdW.

12. The method of claim 11, wherein said microorganism further presents a deletion of the gene aceK.

13. The method of claim 1, wherein said heterologous inducible promoter is a promoter regulated by a modified repressor of phage lambda.

14. The method of claim 1, wherein said heterologous inducible promoter is a modified lac promoter regulated by a temperature sensitive lac repressor.

15. The method of claim 1, wherein said heterologous inducible promoter is a promoter having activity that is modulated with chemical external stimulus.

16. The method of claim 3, wherein said temperature labile allele of a lambda repressor cI comprises lambda repressor allele cI857.

* * * * *

SEQUENCE LISTING

<160> NUMBER OF SEQ ID NOS: 20

<210> SEQ ID NO 1
<211> LENGTH: 128
<212> TYPE: DNA
<213> ORGANISM: Artificial Sequence
<220> FEATURE:
<223> OTHER INFORMATION: Oligonucleotide

<400> SEQUENCE: 1
gcaagctagc tcactcgttg agaggaagac gaaaatgact ccgtttatga ctgaagattt    60
cctgttagat accgtcacac tggctcacct tcgggtgggc ctttctgctg taggctggag   120
ctgcttcg                                                            128

<210> SEQ ID NO 2
<211> LENGTH: 129
<212> TYPE: DNA
<213> ORGANISM: Artificial Sequence
<220> FEATURE:
<223> OTHER INFORMATION: Oligonucleotide

<400> SEQUENCE: 2
ttaacaactc atttcgactt tatagcgtta cgccgctttt gaagatcgcc gaattcgagc    60
tcggtacccg gggatccatc tcgagatccg cggatgtata catgggcccc atatgaatat   120
cctccttag                                                           129

<210> SEQ ID NO 3
<211> LENGTH: 24
<212> TYPE: DNA
<213> ORGANISM: Artificial Sequence
<220> FEATURE:
<223> OTHER INFORMATION: Oligonucleotide

<400> SEQUENCE: 3
cccactggcc tgtaatatgt tcgg                                           24

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide

<400> SEQUENCE: 4
atgcgatatc gaccgtataa gcagcagaat aggc                                34

<210> SEQ ID NO 5
<211> LENGTH: 110
<212> TYPE: DNA
<213> ORGANISM: Artificial Sequence
<220> FEATURE:
<223> OTHER INFORMATION: Oligonucleotide

<400> SEQUENCE: 5
gcctacaggg cccgtatact aaaaataaga gttaccttaa atggtaactc ttatttttt    60 tatcagccaa acgtctcttc aggccactga ctagcgataa ctttccccac               110

<210> SEQ ID NO 6
<211> LENGTH: 93
<212> TYPE: DNA
<213> ORGANISM: Artificial Sequence
<220> FEATURE:
<223> OTHER INFORMATION: Oligonucleotide

<400> SEQUENCE: 6
gccttgtgcc ggaacaacta ctttactttc catttataac ctccttagta catgcaacca    60
ttatcaccgc cagaggtaaa atagtcaaca cgc                                 93

<210> SEQ ID NO 7

<211> LENGTH: 93
<212> TYPE: DNA
<213> ORGANISM: Artificial Sequence
<220> FEATURE:
<223> OTHER INFORMATION: Oligonucleotide

<400> SEQUENCE: 7
gcgtgttgac tattttacct ctggcggtga taatggttgc atgtactaag gaggttataa    60
atggaaagta aagtagttgt tccggcacaa ggc                                 93

<210> SEQ ID NO 8
<211> LENGTH: 91
<212> TYPE: DNA
<213> ORGANISM: Artificial Sequence
<220> FEATURE:
<223> OTHER INFORMATION: Oligonucleotide

<400> SEQUENCE: 8
ctagatatca acagataaaa cgaaaggccc agtctttcga ctgagccttt cgttttattt    60
gatgttacat gttttcgatg atcgcgtcac c                                   91

<210> SEQ ID NO 9
<211> LENGTH: 105
<212> TYPE: DNA
<213> ORGANISM: Artificial Sequence
<220> FEATURE:
<223> OTHER INFORMATION: Oligonucleotide

<400> SEQUENCE: 9 ctaaagaag ttttttgcat ggtattttca gagattatga attgccgcat ttcacactgg    60
ctcaccttcg ggtgggcctt tctgctgtag gctggagctg cttcg                   105

<210> SEQ ID NO 10
<211> LENGTH: 50
<212> TYPE: DNA
<213> ORGANISM: Artificial Sequence
<220> FEATURE:
<223> OTHER INFORMATION: Oligonucleotide

<400> SEQUENCE: 10
caccgccaga ggtaaaatag tcaacacgca cggtgttaga tatttatccc                50

<210> SEQ ID NO 11
<211> LENGTH: 50
<212> TYPE: DNA
<213> ORGANISM: Artificial Sequence
<220> FEATURE:
<223> OTHER INFORMATION: Oligonucleotide

<400> SEQUENCE: 11
gggataaata tctaacaccg tgcgtgttga caattttacc tctggcggtg                50

<210> SEQ ID NO 12
<211> LENGTH: 36
<212> TYPE: DNA
<213> ORGANISM: Artificial Sequence
<220> FEATURE:
<223> OTHER INFORMATION: Oligonucleotide

<400> SEQUENCE: 12
gggataatcg gattttcagg aacgttgagt ttgccg                               36

<210> SEQ ID NO 13
<211> LENGTH: 102

<212> TYPE: DNA
<213> ORGANISM: Artificial Sequence
<220> FEATURE:
<223> OTHER INFORMATION: Oligonucleotide

<400> SEQUENCE: 13
gccgcgtggc ctggaattat tgattgctca aaccattttg caaggcttcg atgctcagta    60
tggtcgattc ctcgaagtga ccaattaacc ctcactaaag gg    102

<210> SEQ ID NO 14
<211> LENGTH: 99
<212> TYPE: DNA
<213> ORGANISM: Artificial Sequence
<220> FEATURE:
<223> OTHER INFORMATION: Oligonucleotide

<400> SEQUENCE: 14
aacatcttcc acatgccctt cacgtatgcg gttttgtagt gcgcgccagt aatcagcgcg    60
gaacaggtcg gcgtgcatct aatacgactc actataggg    99

<210> SEQ ID NO 15
<211> LENGTH: 21
<212> TYPE: DNA
<213> ORGANISM: Artificial Sequence
<220> FEATURE:
<223> OTHER INFORMATION: Oligonucleotide

<400> SEQUENCE: 15
ggtgtggtgg aaaattcgtc g    21

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide

<400> SEQUENCE: 16
gcattacgat tgcccatacc    20

<210> SEQ ID NO 17
<211> LENGTH: 21
<212> TYPE: DNA
<213> ORGANISM: Artificial Sequence
<220> FEATURE:
<223> OTHER INFORMATION: Oligonucleotide

<400> SEQUENCE: 17
cagagattat gaattgccgc a    21

<210> SEQ ID NO 18
<211> LENGTH: 21
<212> TYPE: DNA
<213> ORGANISM: Artificial Sequence
<220> FEATURE:
<223> OTHER INFORMATION: Oligonucleotide

<400> SEQUENCE: 18
ccaggagatt ttacgctcgc c    21

<210> SEQ ID NO 19
<211> LENGTH: 27
<212> TYPE: DNA
<213> ORGANISM: Artificial Sequence
<220> FEATURE:

```
<223> OTHER INFORMATION: Oligonucleotide

<400> SEQUENCE: 19
aacgcattac ccactctgtt taatacg                                              27

<210> SEQ ID NO 20
<211> LENGTH: 19
<212> TYPE: DNA
<213> ORGANISM: Artificial Sequence
<220> FEATURE:
<223> OTHER INFORMATION: Oligonucleotide

<400> SEQUENCE: 20
cttatcatgc ctacagccg                                                       19
```